US010614285B2

(12) United States Patent
West et al.

(10) Patent No.: US 10,614,285 B2
(45) Date of Patent: Apr. 7, 2020

(54) COMPUTING TECHNOLOGIES FOR IMAGE OPERATIONS

(71) Applicant: PROSCIA, Inc., Haverford, PA (US)

(72) Inventors: David R. West, Haverford, PA (US); Coleman C. Stavish, Havertown, PA (US); Max Yeo, New York, NY (US); Brian H. Jackson, Poquoson, VA (US); William Hang, San Diego, CA (US)

(73) Assignee: PROSCIA INC., Philadelphia, PA (US)

(*) Notice: Subject to any disclaimer, the term of this patent is extended or adjusted under 35 U.S.C. 154(b) by 144 days.

(21) Appl. No.: 15/557,317

(22) PCT Filed: Mar. 17, 2016

(86) PCT No.: PCT/US2016/022807
§ 371 (c)(1),
(2) Date: Sep. 11, 2017

(87) PCT Pub. No.: WO2016/149468
PCT Pub. Date: Sep. 22, 2016

(65) Prior Publication Data
US 2019/0073510 A1    Mar. 7, 2019

Related U.S. Application Data

(60) Provisional application No. 62/135,118, filed on Mar. 18, 2015, provisional application No. 62/135,111, filed on Mar. 18, 2015.

(51) Int. Cl.
*G06K 9/00* (2006.01)
*G06K 9/62* (2006.01)
(Continued)

(52) U.S. Cl.
CPC ......... *G06K 9/0014* (2013.01); *G06K 9/6253* (2013.01); *G06T 7/0012* (2013.01);
(Continued)

(58) Field of Classification Search
CPC .... G06K 9/0014; G06K 9/6253; G16B 40/00; G16B 50/00; G06T 7/0012; G06T 2207/10056
(Continued)

(56) References Cited

U.S. PATENT DOCUMENTS 8,712,142 B2 * 4/2014 Rajpoot ............... G06T 7/0012
382/134
9,430,830 B2 * 8/2016 Madabhushi ......... G06T 7/0012
(Continued)

FOREIGN PATENT DOCUMENTS

WO    WO 2012/061452 A1    5/2012
WO    WO 2015/054666 A1    4/2015

OTHER PUBLICATIONS

Young, Lee W., (PCT Officer), "PCT International Search Report and Written Opinion of the International Searching Authority," dated Jun. 16, 2016, 7 pages.

*Primary Examiner* — Jonathan S Lee
(74) *Attorney, Agent, or Firm* — MH2 Technology Law Group LLP

(57) ABSTRACT

A method comprises: receiving, via a processor, an image depicting a tissue; quantifying, via the processor, the image based on: segmenting, via the processor, the image into a plurality of segments; identifying, via the processor, a plurality of histological elements in the segments; forming, via the processor, a network graph comprising a plurality of nodes, wherein the histological elements correspond to the nodes; measuring, via the processor, a feature of the network graph; performing, via the processor, a transformation on the image based on the feature; determining, via the processor, a non-parametric feature of the image based on the transformation; saving, via the processor, the non-parametric feature onto a database.

13 Claims, 18 Drawing Sheets

(51) Int. Cl.
*G16B 40/00* (2019.01)
*G16B 50/00* (2019.01)
*G06T 7/00* (2017.01)

(52) U.S. Cl.
CPC .............. *G16B 40/00* (2019.02); *G16B 50/00* (2019.02); *G06T 2207/10056* (2013.01)

(58) Field of Classification Search
USPC ......................................................... 382/173
See application file for complete search history.

(56) References Cited

U.S. PATENT DOCUMENTS

| | | |
|---|---|---|
| 2006/0204953 A1 | 9/2006 | Ptitsyn |
| 2010/0077358 A1 | 3/2010 | Sugaya |
| 2010/0111396 A1* | 5/2010 | Boucheron .......... G06K 9/0014 |
| | | 382/133 |
| 2010/0138422 A1 | 6/2010 | Mattiuzzi |
| 2010/0290692 A1 | 11/2010 | Macaulay et al. |
| 2011/0252000 A1 | 10/2011 | Diaconu et al. |
| 2012/0106821 A1* | 5/2012 | Madabhushi ......... G06T 7/0012 |
| | | 382/133 |
| 2013/0071003 A1 | 3/2013 | Wirtz et al. |
| 2014/0233826 A1 | 8/2014 | Agaian et al. |

* cited by examiner

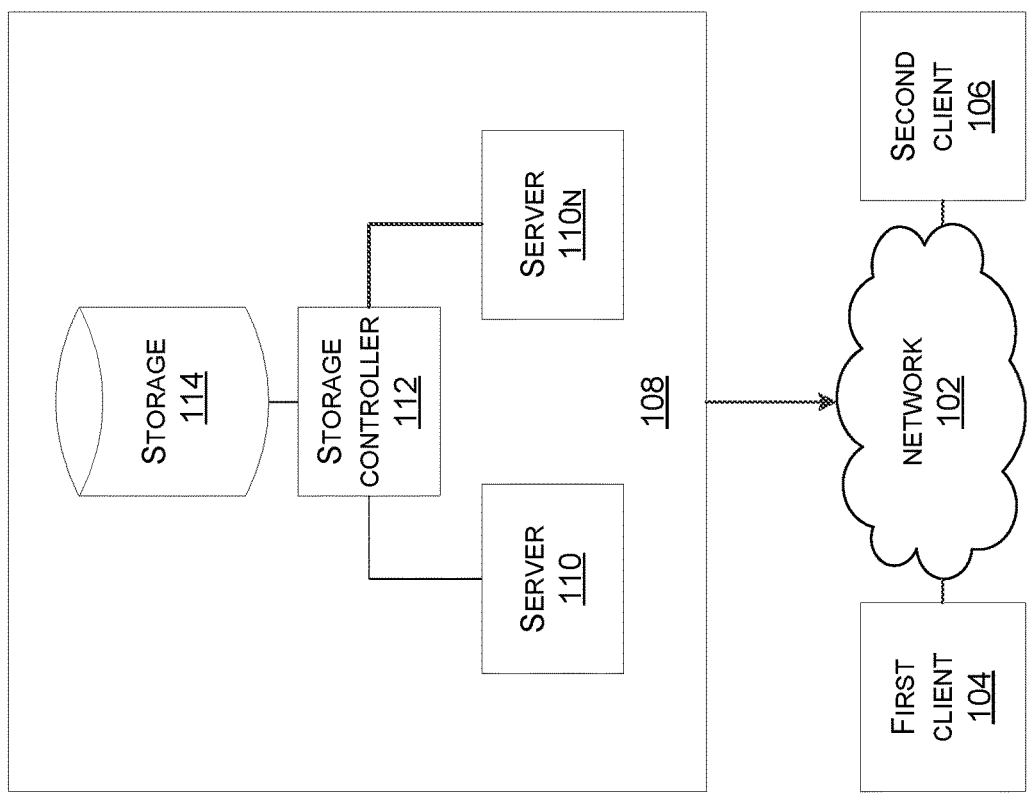

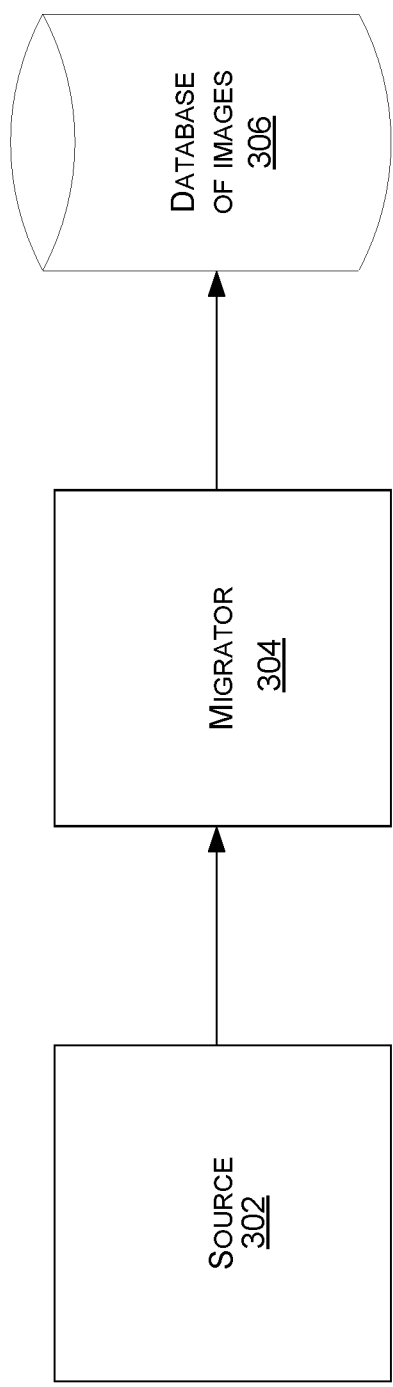

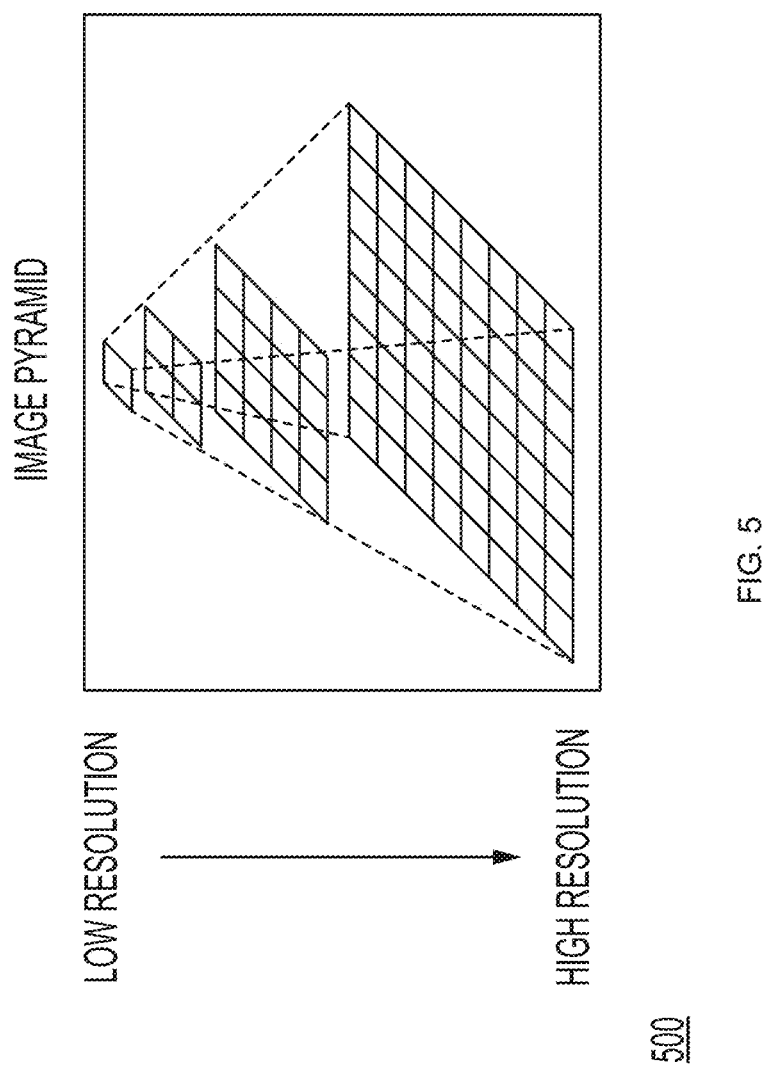

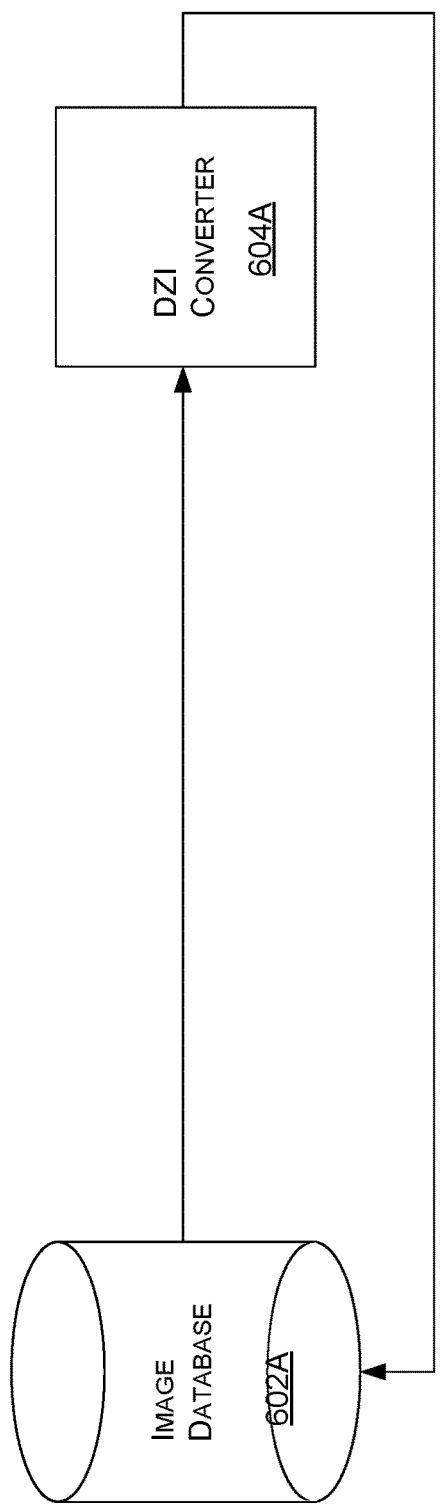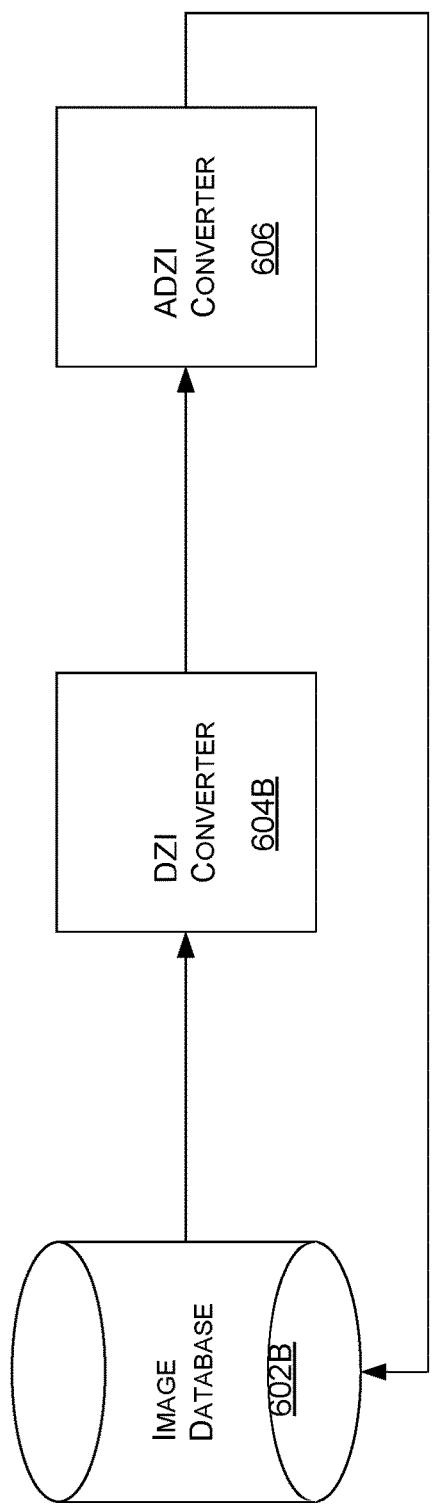

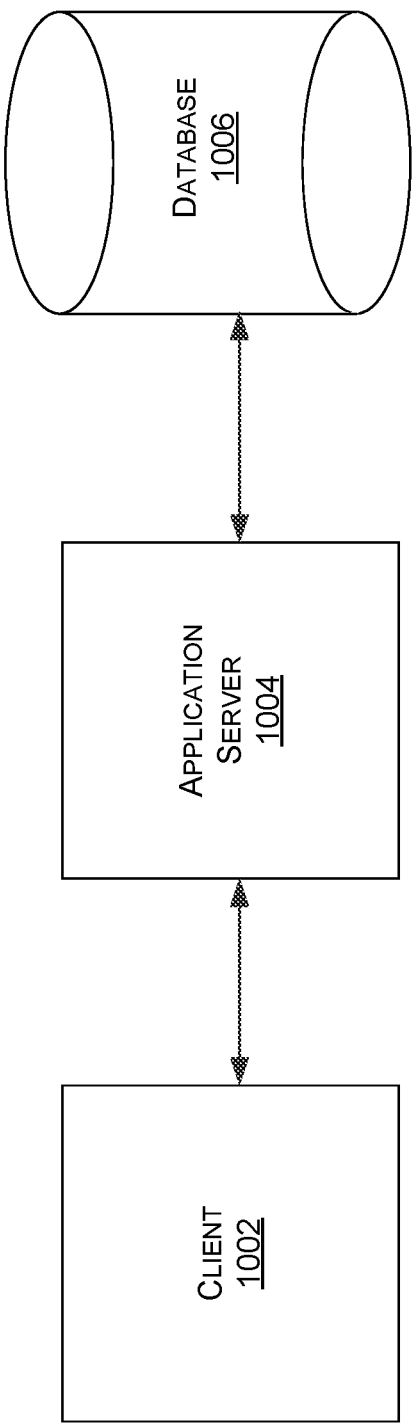

| File Name | ☐ | × Nucleus Area-MEAN | ⇕ | × Nuclear Perimeter-MEAN | ⇕ | × Nuclear Perimeter-VARIANCE | ⇕ | × Mean Gray Value-VARIANCE |
|---|---|---|---|---|---|---|---|---|
| ☐ TMA_0471_HE_02_1.tif | | 34.1940204971061 | | 4.9226938343448002 | | 34.1317709360828 | | 199.828639763021 |
| ☐ TMA_0471_HE_02_2.tif | | 44.4982014388489 | | 5.8519197070535597 | | 39.0236807016126 | | 105.422146803693 |
| ☐ TMA_0471_HE_03_1.tif | | 35.6380133711537 | | 5.3066351483402 | | 41.1578812663664 | | 74.039879116318 |
| ☐ TMA_0471_HE_03_2.tif | | 34.7334630350195 | | 5.518754853813253 | | 56.3075173381154 | | 98.687267013471153 |
| ☐ TMA_0471_HE_04_1.tif | | 49.9725430198076 | | 6.3125470885735353 | | 27.0625768898582 | | 118.35711186814 |
| ☐ TMA_0471_HE_04_2.tif | | 49.6188693965742 | | 5.1718249733191 | | 35.3725588831317 | | 118.498299810908 |
| ☐ TMA_0471_HE_05_1.tif | | 60.5497142857143 | | 4.856 | | 25.7763988006795 | | 60.8407603994976 |
| ☐ TMA_0471_HE_05_2.tif | | 45.5473987814315 | | 4.8634226597698992 | | 23.3717187119443 | | 62.11780322892.9 |
| ☐ TMA_0471_HE_06_1.tif | | 45.5240847842 | | 4.775480325626204 | | 22.8445708030086 | | 105.5039769653931 |
| ☐ TMA_0471_HE_06_2.tif | | 53.7568693552354 | | 5.5917159753136 | | 36.5968354040307 | | 159.656443317.128 |
| ☐ TMA_0471_HE_07_1.tif | | 48.4428719546479 | | 5.9252133899202 | | 40.7636673711103 | | 86.4838347346794 |
| ☐ TMA_0471_HE_07_2.tif | | 51.1105292348676 | | 6.1603084223131 | | 42.1249812333291 | | 95.978421392 |
| ☐ TMA_0471_HE_08_1.tif | | 34.9422688422688 | | 5.051083061933065 | | 22.236014392534 | | 139.627362297493 |
| ☐ TMA_0471_HE_08_2.tif | | 88.3710054558635 | | 5.3312548713951 | | 26.1623211381179 | | 137.515795340197 |
| ☐ TMA_0471_HE_09_1.tif | | 48.223532815 | | 5.56984375 | | 31.163397607610 | | 125.5242271466.22 |
| ☐ TMA_0471_HE_09_2.tif | | 36.4515630918383 | | 4.7240370815942 | | 19.0498358298044 | | 101.479898063372 |
| ☐ TMA_0471_HE_10_1.tif | | 55.933762337862 | | 6.631168861633 | | 49.663818447881 | | 107.25070314861 |

COMPUTING TECHNOLOGIES FOR IMAGE OPERATIONS

CROSS-REFERENCE TO RELATED APPLICATIONS

This application is a U.S. National Phase application of PCT/US2016/022807 filed 17 Mar. 2016, which claims the benefit of U.S. Provisional Patent Application 62/135,118 filed 18 Mar. 2015, and U.S. Provisional Application 62/135,111 filed 18 Mar. 2015; each of which is hereby incorporated by reference herein for all purposes.

TECHNICAL FIELD

Generally, the present disclosure relates to computing. More particularly, the present disclosure relates to network-based image services.

BACKGROUND

In the present disclosure, where a document, an act and/or an item of knowledge is referred to and/or discussed, then such reference and/or discussion is not an admission that the document, the act and/or the item of knowledge and/or any combination thereof was at the priority date, publicly available, known to the public, part of common general knowledge and/or otherwise constitutes prior art under the applicable statutory provisions; and/or is known to be relevant to an attempt to solve any problem with which the present disclosure is concerned with. Further, nothing is disclaimed.

Pathology is a field of science which deals with laboratory examinations of samples of tissue for diagnostic, research, forensic, academic, or other purposes. Pathologists, as well others working in medical or biological research, examine human, animal, floral, or other tissue to assess disease state or understand biological features. In one aspect of pathology, a tissue is biopsied from a patient for analysis and fixed on a glass slide to be viewed under a light microscope. However, such form of tissue assessment is disadvantageous for various reasons. For example, some of such disadvantages include subjectivity and low throughput.

With respect to the subjectivity, a purely human analysis of tissue suffers from low inter-pathologist concordance rates and low intra-pathologist concordance rates. The inter-pathologist concordance refers to an ability of different human pathologists to agree on an assessment (typically diagnostic or prognostic assessment) of a same biopsy. The intra-pathologist concordance refers to an ability of a single pathologist to reproduce his/her assessment of a same tissue section at two separate times. For example, according to Hu, Fei, Nikita V. Orlav, and Ilya G. Goldberg, Telehealthcare Computing and Engineering: Principles and Design, 2013, Print, "Traditional pathology is based on manual assessments of tissue sections under a microscope. A common problem with that approach is the inconsistency of readings across different readers and even by the same reader. Another common problem is that a high-quality diagnosis often requires analyzing multiple samples from the same patient independently, which is challenging with a single reader. Manual readers faced with many similar samples can also experience fatigue, adding to the inconsistency of the readings." (Hu, Fei, Nikita V. Orlav, and Ilya G. Goldberg. Telehealthcare Computing and Engineering: Principles and Design).

With respect to the low throughput, an unnecessary amount of time spent on analysis of tissue by a human reader. For example, according to Gurcan, Metin N. et al. "Histopathological Image Analysis: A Review." IEEE reviews in biomedical engineering 2 (2009): 147-171. PMC. Web. 24 Feb. 2015, "approximately 80% of the 1 million prostate biopsies performed in the US every year are benign; this suggests that prostate pathologists are spending 80% of their time sieving through benign tissue". However, in a past decade, digitally scanned slides have enabled computer-based technologies to be applied to pathology. By scanning tissue slides into digital images using specialized scanners, some aspects of storage, viewing, analysis, and assessment of tissue samples can be aided by digital approaches.

The past decade has brought promising developments in pathology. While those in biology or medicine have been restricted to the light microscope for inspection of glass slides, whole-slide imaging (WSI) has offered a radically different medium for understanding human tissue or other biological tissues. WSI scanners create high-resolution digital images of glass slides and differ from cameras attached to or integrated with microscopes in that, while a camera captures a static snapshot of a slide of a single area at a fixed magnification, a WSI scanner scans across the slide at every magnification power (typically up to 40×), and stitches together various images into terabyte-scale files. Accordingly, various implications of slide digitization in pathology are profound and extend beyond one or more benefits of simply migrating workflows from an optical lens to a display. Technology and research are being applied to many components of such digital workflow chain. Though currently largely fragmented and underdeveloped, this digital workflow chain includes scanning, storage (and cloud migration), viewing and integration, computing/processing, image analysis, machine learning, and diagnostics.

While WSI scanning is peaking in technological maturity, an infrastructure for moving, storing, accessing, and processing medical image as large as biopsy scans is weak. For example, server infrastructure to manage digital pathology data is costly. Therefore, in order to store many terabytes of medical images entails additional information technology (IT) administrators, software for management and retrieval, servers, redundant storage clusters, data, backup, security, and recovery services, many of which can cost millions of dollars per year. Since hospitals and commercial pathology labs are not IT businesses, there is a need for computing systems which can provide cloud storage and image access systems at orders of magnitude cheaper than currently available in-house alternatives.

Additionally, while some analysis methods for tissue images may be mathematically and histologically sound, there remain some logistical or implementational problems. For example, due to a fact that some digital biopsy images are in extremely high-resolution and therefore, large in units of information, in many instances, such images mandate several gigabytes of storage space. Also, another consequence of such large image size is a significant processing time involved to perform some quantitative analysis. Therefore, long processing times may preclude conclusions from having any clinical significance, where the conclusions may be drawn from a quantitative image analysis. Therefore, some of such quantitative analysis is desired to be performed in real-time, or in near real-time. Further, due to a high number of biopsies excised, stained, and scanned per year, a computing system that aims to serve as a clinical aid should be able to process a large volume of images at any given time, without suffering significant performance drops. Additionally, some results of the quantitative image analysis may lose utility or value if such results are discarded after calculation. If the quantitative image analysis results are subsequently not stored in an effective way, then, if the computing system employs models, then such models cannot be effectively trained to make clinical judgments. Therefore, there is a need for a robust, well-defined, and highly accessible computing system which is capable of storing quantitative analysis results in an efficient manner.

BRIEF SUMMARY

The present disclosure at least partially addresses at least one of the above drawbacks of conventional systems. However, the present disclosure can prove useful to other technical areas. Therefore, the claims should not be construed as necessarily limited to addressing any of the above.

In an embodiment, a method comprises: receiving, via a processor, an image depicting a tissue; quantifying, via the processor, the image based on: segmenting, via the processor, the image into a plurality of segments; identifying, via the processor, a plurality of histological elements in the segments; forming, via the processor, a network graph comprising a plurality of nodes, wherein the histological elements correspond to the nodes; measuring, via the processor, a feature of the network graph; performing, via the processor, a transformation on the image based on the feature; determining, via the processor, a non-parametric feature of the image based on the transformation; saving, via the processor, the non-parametric feature onto a database.

Additional features and advantages of various embodiments are set forth in the description which follows, and in part is apparent from the description. Various objectives and other advantages of the present disclosure are realized and attained by various structures particularly pointed out in the exemplary embodiments in the written description and claims hereof as well as the appended drawings. It is to be understood that both the foregoing general description and the following detailed description are exemplary and explanatory and are intended to provide further explanation of the present disclosure as claimed.

INCORPORATION BY REFERENCE

Hereby, all issued patents, published patent applications, and non-patent publications which are mentioned in this specification are herein fully incorporated by reference for all purposes, to a same extent as if each individual issued patent, published patent application, or non-patent publication were specifically and individually indicated to be incorporated by reference.

BRIEF DESCRIPTION OF DRAWINGS

The accompanying drawings constitute a part of this specification and illustrate an embodiment of the present disclosure and together with the specification, explain the present disclosure.

FIG. 1 shows a schematic view of an embodiment of a network topology according to the present disclosure.

FIG. 3 shows a schematic view of an embodiment of a migration topology according to the present disclosure.

FIG. 5 shows a schematic diagram of an embodiment of a conversion architecture according to the present disclosure.

FIG. 6A shows a schematic diagram of a system to convert an image according to the present disclosure.

FIG. 6B shows a schematic diagram of a system to convert an image according to the present disclosure.

FIG. 10 shows a schematic view of a delivery topology according to the present disclosure.

FIG. 13 shows an example embodiment of a user console comprising a data table according to the present disclosure.

FIG. 15 shows an example embodiment of a user console comprising a run control tool according to the present disclosure.

DETAILED DESCRIPTION OF PREFERRED EMBODIMENTS

Figure 2C:
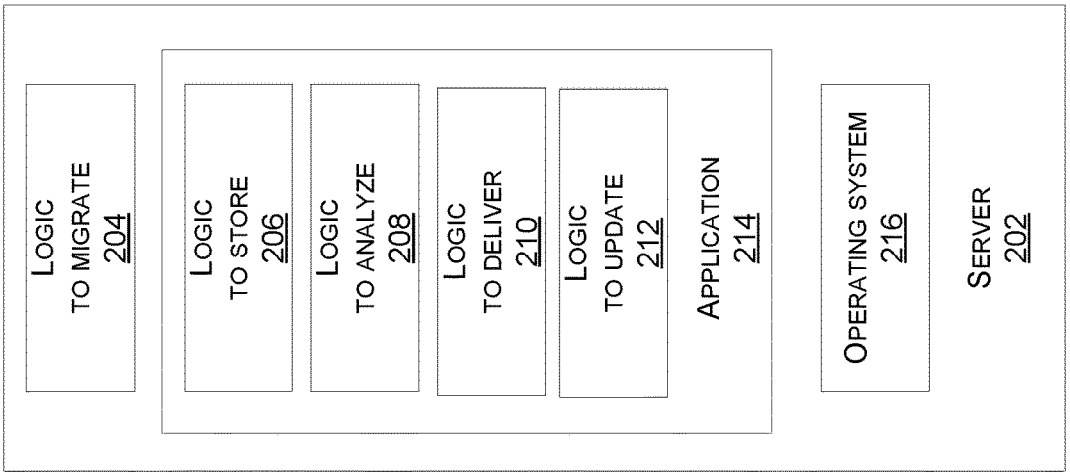
FIGS. 2A-2C shows schematic views of embodiments of logic distribution according to the present disclosure.

The present disclosure is now described more fully with reference to the accompanying drawings, in which embodiments of the present disclosure are shown. The present disclosure may, however, be embodied in many different forms and should not be construed as necessarily being limited to the embodiments disclosed herein. Rather, these embodiments are provided so that the present disclosure is thorough and complete, and fully conveys the concepts of the present disclosure to those skilled in the relevant art.

Features or functionality described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity or actor in any manner.

The terminology used herein can imply direct or indirect, full or partial, temporary or permanent, action or inaction. For example, when an element is referred to as being "on,"

"connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

Furthermore, relative terms such as "below," "lower," "above," and "upper" can be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings were turned over, then the elements described as being on the "lower" side of other elements would then be oriented on "upper" sides of the other elements. Similarly, if the device in one of the figures were turned over, elements described as "below" or "beneath" other elements would then be oriented "above" the other elements. Therefore, the example terms "below" and "lower" can encompass both an orientation of above and below.

The terminology used herein is for describing particular example embodiments and is not intended to be necessarily limiting of the present disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence and/or addition of one or more other features, integers, steps, operations, elements, components, and/or groups thereof.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

As used herein, the term "about" and/or "substantially" refers to a +/−10% variation from the nominal value/term. Such variation is always included in any given.

If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls FIG. 1 shows a schematic view of an embodiment of a network topology according to the present disclosure. A network topology 100 comprises a network 102, a first client 104, a second client 106, a computing system 108, a server 110, a data storage controller 112, and a data storage 114. Any or all components of the topology 100 can be coupled, as shown, directly or indirectly, whether in a wired or a wireless manner. Note that each of components of the topology 100 can be implemented in logic, whether hardware-based or software-based. For example, when the logic is hardware-based, then such logic can comprise circuitry, such as processors, memory, input devices, output devices, or other hardware, that is configured, such as via programming or design, to implement a functionality of a respective component. Likewise, when the logic is software-based, then such logic can comprise one or more instructions, such as assembly code, machine code, object code, source code, or any other type of instructions, which when executed, such as via running or compilation, implement a functionality of a respective component. Further, note that at least one of such components can be implemented as a service. Moreover, note that at least two of such components can be hosted on one computing system/hardware/device or each be distinctly hosted.

The topology 100 is based on a distributed network operation model which allocates tasks/workloads between servers, which provide a resource/service, and clients, which request the resource/service. The servers and the clients illustrate different computers/applications, but in some embodiments, the servers and the clients reside in or are one system/application. Further, in some embodiments, the topology 100 entails allocating a large number of resources to a small number of computers, such as the server 110, where complexity of the clients, such as the clients 104, 106, depends on how much computation is offloaded to the small number of computers, i.e., more computation offloaded from the clients onto the servers leads to lighter clients, such as being more reliant on network sources and less reliant on local computing resources. Note that other computing models are possible as well. For example, such models can comprise decentralized computing, such as peer-to-peer (P2P), for instance Bit-Torrent®, or distributed computing, such as via a computer cluster where a set of networked computers works together such that the computer can be viewed as a single system.

The network 102 includes a plurality of nodes, such as a collection of computers and/or other hardware interconnected via a plurality of communication channels, which allow for sharing of resources and/or information. Such interconnection can be direct and/or indirect. The network 102 can be wired and/or wireless. The network 102 can allow for communication over short and/or long distances, whether encrypted and/or unencrypted. The network 102 can operate via at least one network protocol, such as Ethernet, a Transmission Control Protocol (TCP)/Internet Protocol (IP), and so forth. The network 102 can have any scale, such as a personal area network (PAN), a local area network (LAN), a home area network, a storage area network (SAN), a campus area network, a backbone network, a metropolitan area network, a wide area network (WAN), an enterprise private network, a virtual private network (VPN), a virtual network, a satellite network, a computer cloud network, an internetwork, a cellular network, and so forth. The network 102 can be and/or include an intranet and/or an extranet. The network 102 can be and/or include Internet. The network 102 can include other networks and/or allow for communication with other networks, whether sub-networks and/or distinct networks, whether identical and/or different from the network 102 in structure or operation. The network 102 can include hardware, such as a computer, a network interface card, a repeater, a hub, a bridge, a switch, an extender, an antenna, and/or a firewall, whether hardware based and/or software based. The network 102 can be operated, directly and/or indirectly, by and/or on behalf of one and/or more entities or actors, irrespective of any relation to contents of the present disclosure.

At least one of the clients 104, 106 can be hardware-based and/or software-based. At least one of the clients 104, 106 is and/or is hosted on, whether directly and/or indirectly, a client computer, whether stationary or mobile, such as a terminal, a kiosk, a workstation, a vehicle, whether land, marine, or aerial, a desktop, a laptop, a tablet, a mobile phone, a mainframe, a supercomputer, a server farm, and so forth. The client computer can comprise another computer system and/or cloud computing network. The client computer can run any type of operating system (OS), such as MacOS®, Windows®, Android®, Unix®, Linux® and/or others. The client computer can include and/or be coupled to an input device, such as a mouse, a keyboard, a camera, whether forward-facing and/or back-facing, an accelerometer, a touchscreen, a biometric reader, a clicker, a microphone, a transceiver, or any other suitable input device. The client computer can include and/or be coupled to an output device, such as a display, a speaker, a headphone, a joystick, a vibrator, a printer, a transceiver, or any other suitable output device. In some embodiments, the input device and the output device can be embodied in one unit, such as a touch-enabled display, which can be haptic. The client computer can include circuitry, such as a receiver chip, for geolocation/global positioning determination, such as via a global positioning system (GPS), a signal triangulation system, and so forth. The client computer can be equipped with near-field-communication (NFC) functionality, such as via an NFC chip. The client computer can host, run and/or be coupled to, whether directly and/or indirectly, a database, such as a relational database or a non-relational database, such as a post-relational database, an in-memory database, or others, which can feed or otherwise provide data to at least one of the clients 104, 106, whether directly and/or indirectly.

At least one of the clients 104, 106, via the client computer, is in communication with network 102, such as directly and/or indirectly, selectively and/or unselectively, encrypted and/or unencrypted, wired and/or wireless, via contact and/or contactless. Such communication can be via a software application, a software module, a mobile app, a browser, a browser extension, an OS, and/or any combination thereof. For example, such communication can be via a common or standardized framework/Application Programming Interface (API), such as Hypertext Transfer Protocol Secure (HTTPS). In some embodiments, the computing system 108, such as via the server 110, and at least one of the clients 104, 106 can directly communicate with each other, such as when hosted in one system or when in local proximity to each other, such as via a short range wireless communication protocol, such as infrared or Bluetooth®. Such direct communication can be selective and/or unselective, encrypted and/or unencrypted, wired and/or wireless, via contact and/or contactless. Since the clients 104, 106 can initiate sessions with the computing system 108, such as via the server 110, relatively simultaneously, in some embodiments, the computing system 108, such as via the server 110, employs load-balancing technologies and/or failover technologies for operational efficiency, continuity, and/or redundancy.

The computing system 108 comprises the server 110, the storage controller 112, and the storage 114, with the storage controller 112 being communicably interposed, whether directly or indirectly, between the server 110 and the storage 114. Note that the computing system 108 can comprise any number of servers 110, such as servers 110$n$, storage controllers 112, and storages 114 in any combinatory or permutational manner. For example, the computing system 108 can distribute a functionality, such as storage, or run an application, in whole or in part, among a plurality or a cluster of servers 110-110$n$, which can be on-demand or dynamically adjustable based on resource utilization/scaling. For example, at least one of servers 110$n$ can comprise a graphics processing unit (GPU). Accordingly, a cluster of GPUs can be used.

The server 110 can be hardware-based and/or software-based. The server 110 is and/or is hosted on, whether directly and/or indirectly, a server computer, whether stationary or mobile, such as a kiosk, a workstation, a vehicle, whether land, marine, or aerial, a desktop, a laptop, a tablet, a mobile phone, a mainframe, a supercomputer, a server farm, and so forth. The server computer can comprise another computer system and/or a cloud computing network. The server computer can run any type of OS, such as MacOS®, Windows®, Android®, Unix®, Linux® and/or others. The server computer can include and/or be coupled to, whether directly and/or indirectly, an input device, such as a mouse, a keyboard, a camera, whether forward-facing and/or back-facing, an accelerometer, a touchscreen, a biometric reader, a clicker, a microphone, a transceiver, or any other suitable input device. The server computer can include and/or be coupled to, whether directly and/or indirectly, an output device, such as a display, a speaker, a headphone, a vibrator, a printer, a transceiver, or any other suitable output device. In some embodiments, the input device and the output device can be embodied in one unit, such as a touch-enabled display, which can be haptic. The server computer can include circuitry, such as a receiver chip, for geolocation/ global positioning determination, such as via a GPS, a signal triangulation system, and so forth. The server computer can be equipped with NFC circuitry, such as an NFC chip. The server computer can host, run, and/or be coupled to, whether directly and/or indirectly, a database, such as a relational database or a non-relational database, such as a post-relational database, an in-memory database, or others, which can feed, avail, or otherwise provide data to at least one of the server 110, whether directly and/or indirectly. The server 110 or the servers 110$n$ can comprise at least one of a network server, an application server, or a database server. In some embodiments, the server 110 can be task-dedicated. In some embodiments, at least two of the servers 110 can be a single server, such as a database server and an application server.

For example, the network server can be configured to serve content, such as a network page, to the application server in response receiving a corresponding request. Such service can be via a protocol, such as Hypertext Transfer Protocol (HTTP). For example, the network page can be file-based and can be static or dynamically generated, such as Hypertext Transfer Markup Language (HTML). For example, the network server can comprise a web server, such as Apache, Microsoft's Internet Information Server (IIS), Novell's NetWare server, Google Web Server (GWS), or IBM Domino server.

For example, the application server hosts a software application and a set of logic for the software application, such as a set of rules. Therefore, as instructed by respective software application, the application server can communicably interface with the network server and the database server. For example, the application server can act as a middle-tier server, with the network server acting as a front-tier server, and the database server acting as a back-end server. For example, the application server can be an IBM WebSphere application server or a SAP Web application server. In some embodiments, the application server can comprise a plurality of independent cores, such as a multi-core processor comprising a computing component with two or more independent processing units, which are the units that read and execute program instructions, such as via multiprocessing or multithreading. The instructions are processing instructions, such as add, move data, or branch, but the cores can run multiple instructions concurrently, thereby increasing an overall operational speed for the software application, which can be amenable to parallel computing. The cores can process in parallel when concurrently accessing a file or any other data structure, as disclosed herein, while being compliant with atomicity, consistency, isolation, and durability (ACID) principles, which ensure that such data structure operations/transactions, such as read, write, erase, or others, are processed reliably. For example, a data structure can be accessed, such as read or written, via at least two cores concurrently, where each of the cores concurrently processes a distinct data structure record or a distinct set of data such that at least two data structure records or at least two sets of the data are processed concurrently, without locking the data structure between such cores. Note that there can be at least two cores, such as two cores, three cores, four cores, six cores, eight cores, ten cores, twelve cores, or more. The cores may or may not share caches, and the cores may or may not implement message passing or shared-memory inter-core communication methods. Common network topologies to interconnect cores include bus, ring, two-dimensional mesh, and crossbar. Homogeneous multi-core systems include only identical cores, heterogeneous multi-core systems can have cores that are not identical. The cores in multi-core systems may implement architectures, such as very long instruction word (VLIW), superscalar, vector, or multithreading.

For example, the database server hosts a database, such as a relational database, a non-relational database, an in-memory database, or others. The database stores data, whether in a raw state, a formatted state, an organized stated, or any other accessible state, and allows access to such data, whether directly and/or indirectly. The database server is configured for various database input (I)/output (O) operations, including reading, writing, editing, deleting, updating, searching, selecting, merging, sorting, erasing, formatting, or others. The database server can implement record locking on the respective database. For example, the database can be an Oracle database, a MS-SQL database, or a DB2 database, as controlled by a relevant database management system.

The storage controller 112 can comprise a device which manages a disk drive or other storage, such as flash storage, and presents the disk drive as a logical unit for subsequent access, such as various data IO operations, including reading, writing, editing, deleting, updating, searching, selecting, merging, sorting, or others. For example, the storage controller 112 can comprise a database management system (DBMS) managing the database. Note that the DBMS can be modifying, in real-time, the storage 114 storing one or more records based. The storage controller 112 can include a front-end side interface to interface with a host adapter of a server and a back-end side interface to interface with a controlled disk storage. The front-end side interface and the back-end side interface can use a common protocol or different protocols. Also, the storage controller 112 can comprise an enterprise controller, which can comprise a physically independent enclosure, such as a disk array of a storage area network or a network-attached storage server. For example, the storage controller 112 can comprise a redundant array of independent disks (RAID) controller. In some embodiments, the storage controller 112 can be lacking such that the storage 114 can be directly accessed by the server 110. In some embodiments, the controller 122 can be unitary with the server 110.

The storage 114 can comprise a storage medium, such as at least one of a data structure, a data repository, a data mart, or a data store. For example, the storage medium comprises a database, such as a relational database, a non-relational database, an in-memory database, such as hosted in a main memory, or others, which can store data, such as in fields, and allow access to such data to the storage controller 112, whether directly and/or indirectly, whether in a raw state, a formatted state, an organized stated, or any other accessible state. For example, the data can comprise image data, sound data, alphanumeric data, or any other data. For example, the storage 114 can comprise a database server. The storage 114 can comprise any type of storage, such as primary storage, secondary storage, tertiary storage, off-line storage, volatile storage, non-volatile storage, semiconductor storage, magnetic storage, optical storage, flash storage, hard disk drive storage, floppy disk drive, magnetic tape, or other data storage medium. The storage 114 is configured for various data I/O operations, including reading, writing, editing, modifying, deleting, updating, searching, selecting, merging, sorting, encrypting, de-duplicating, or others. In some embodiments, the storage 114 can be unitary with the storage controller 112. In some embodiments, the storage 114 can be unitary with the server 110. Note that the storage 114 can be distributed over a plurality of data structures or devices in any combinatory or permutational manner.

In one mode of operation, the computing system 108 comprises a networked, parallel, high-throughput computing infrastructure for image analysis and data storage. The computing system 108 is adaptive and networked, while providing for digital tissue analysis, allowing enhanced accessibility of images, such as digital tissue slide scans and associated data, and maintaining an optimized memory footprint, function modularity, and high scalability. The computing system 108 communicably interfaces with the clients 104, 106 over the network 102. The computing system 108 processes various types of data. For example, the computing system 108 considers several classes of information: images and image-derived data.

Such images comprise data structured in formats that can be interpreted visually by a human, such as a pathologist. For example, the images can be in pixel-based formats or vector formats, but, in some embodiments, the computing system 108 does not distinguish therebetween. Rather, the images depict human, animal, marine, aerial, floral or any other biological tissue in some form. The images may be, but are not limited to, WSI images or static tissue images. The images may be produced by any device, such as, but not limited to a slide scanner, a microscope camera attachment, or a microscope with a built in camera or any other image capture device. In some embodiments, multiple images of a same specimen may be stitched together by computational methods before or within the computing system 108. For example, image file formats may include, but are not limited to, at least one of .tif, .jpeg, .jpg, .png, .bmp, .svs, .vms, .vmu, .npdi, .scn, .mrxs, .tiff, .svslide, .bif, or .dzi. The tissue may be imaged directly from an organism of interest or might by excised from a human, animal, or any other biological being via a surgical biopsy, a fine needle aspiration, or any other technique that allows for tissue sections that can be fixed on a glass slide or digitally captured in some other environment.

The computing system 108 stores non-image data, such as in the storage 114. For example, the non-image data can include a universal identifying case descriptor (UICD), such as a case description identifier, which can be unique. For example, the UICD can comprise alphanumeric information. The UICD may comprise clinical/patient information, image derived data, or usage data. Note that while the image-derived data is derived from images, image-derived data can also be a component of the non-image data, such as the UICD.

Figure 2B:
Figure 2A:
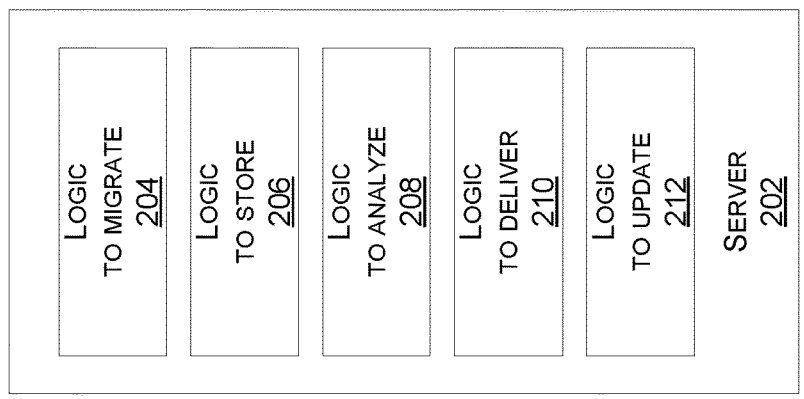

FIGS. 2A-2C shows schematic views of embodiments of logic distribution according to the present disclosure. The computing system 108 is configured to perform a migration functionality, a storage functionality, an analysis functionality, a delivery functionality, and an update functionality. The migration functionality is performed via a logic to migrate 204. The storage functionality is performed via a logic to store 206. The analysis functionality is performed via a logic to analyze 208. The delivery functionality is performed via a logic to deliver 210. The update functionality is performed via a logic to update 212. Each of the logics 204-212 can be hardware-based or software-based. For example, when the logic is hardware-based, then such logic can comprise circuitry, such as processors, memory, input devices, output devices, chips, or other hardware, that is configured, such as via programming or design, to implement a functionality of a respective component. Likewise, when the logic is software-based, then such logic can comprise one or more instructions, such as assembly code, machine code, object code, source code, functions, modules, or any other type of instructions, which when executed, such as via running or compilation, implement a functionality of a respective component. Further, note that at least one of the logics 204-212 can be implemented as a service. Moreover, note that at least two of the logics 204-212 can be hosted on one computing system/hardware/device or each be distinctly hosted.

In FIG. 2A, a server 202, such as the server 110, hosts the logics 204-212. For example, at least one of the logics 204-212 can be a module or a processor-executable set of instructions, such as source code or object code. Note that at least two of the logics 204-212 can be a single logic. Although the logics 204-212 are hosted local to the server 202, at least one of the logics 204-212 can be hosted remote to the server 202.

In FIG. 2B, the server 202, such as the server 110, runs an OS 216 on top of which an application 214 runs. The application 214 includes the logics 204-212. For example, the logics 204-212 can be embodied as modular components or services of the application 214. Note that at least two of the logics 204-212 can be a single logic. Although the logics 204-212 are hosted local to the application 214, at least one of the logics 204-212 can be hosted remote to the server 202, the OS 216, or the application 214.

In FIG. 2C, the server 202, such as the server 110, runs the OS 216 on top of which the application 214 runs. The application 214 includes the logics 204-212. For example, the logics 204-212 can be embodied as modular components or services of the application 214. Note that at least two of the logics 204-212 can be a single logic. Note that the logic 204 is remote to the application 214, yet local to the OS 216 and the server 202. However, note that the logic 204 or any other logic 206-212 can be distributed in any combinatory or permutational manner, whether local to or remote from the server 202, the OS 216, or the application 204.

FIG. 3 shows a schematic view of an embodiment of a migration topology according to the present disclosure. A migration topology 300 comprises a source 302, a migrator 304, and a database of images 306. Any or all components of the topology 300 can be coupled, as shown, directly or indirectly, whether in a wired or a wireless manner, whether local or remote to each other. Note that each of components of the topology 300 can be implemented in logic, whether hardware-based or software-based. For example, when the logic is hardware-based, then such logic can comprise circuitry, such as processors, memory, input devices, output devices, or other hardware, that is configured, such as via programming or design, to implement a functionality of a respective component. Likewise, when the logic is software-based, then such logic can comprise one or more instructions, such as assembly code, machine code, object code, source code, or any other type of instructions, which when executed, such as via running or compilation, implement a functionality of a respective component. Further, note that at least one of such components can be implemented as a service. Moreover, note that at least two of such components can be hosted on one computing system/hardware/device or each be distinctly hosted. For example, the network topology 100 comprises the migration topology 300.

The source 302 may be a local storage device, such as from a storage device that is a component of a hardware upon which the computing system 108 is running, a local-network storage device, such as from a storage device that is not a component of a hardware upon which the computing system 108 is running but instead a remote device accessible over a local network or intranet, or a cloud-based storage service, such as from a remote storage device that may exist in a different geographic region or location than a hardware upon which the computing system 108 is running. The source 302 may be an instance of an application server, such as the server 110, which may have received an image from a client, such as the client 104, 106.

The migrator 304 may be a program running on a computing device, such the server 110. The migrator 304 is connected to the source 302 via a physical connection, such as wiring, or a network connection, such as signal communication. The migrator 304 accepts an image as input from the source 302 and writes the image to the database 306. Note that the image comprises a digital image that is represented in one of a variety of formats, including, but not limited to, .tif, .jpeg, .jpg, .svs, .vms, .vmu, .npdi, .scn, .mrxs, .tiff, .svslide, and .bif.

Figure 4:
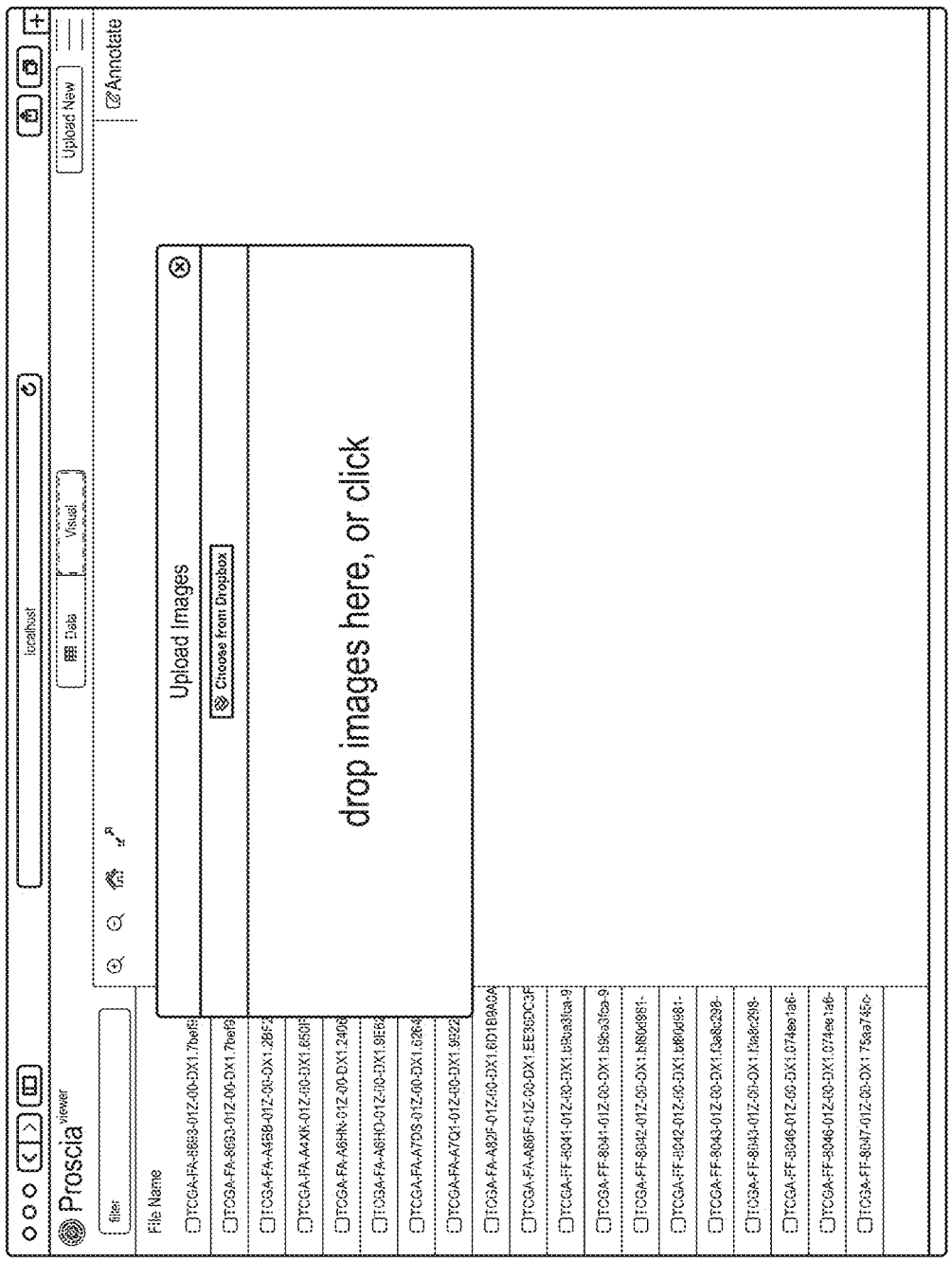
FIG. 4 shows an embodiment of a graphical user interface (GUI) page of providing an image according to the present disclosure.

FIG. 4 shows an embodiment of a GUI page of providing an image according to the present disclosure. A GUI page 400 enables provision of an image, as disclosed herein, such as via the source 302. For example, the client 104, 106 may provide multiple ways by which images and case data can be imported into the computing system 108, including, but not limited to, a local file upload, a remote uniform resource locator (URL) upload, a file transfer protocol (FTP), P2P, an image matching, or an upload via a third party storage provider.

FIG. 5 shows a schematic diagram of an embodiment of a conversion architecture according to the present disclosure. A schematic diagram of a conversion architecture 500 enables an image to be converted into a format which is optimized for viewing in either a native application or a web application over a network connection.

A format optimized for such use cases is a format which uses an image pyramid. In a context of image storage, retrieval, or processing, a pyramid can refer to a manner of multi-scale signal representation. A high resolution source image can be smoothed and down-sampled, such as by a factor of two in both dimensions, yielding a lower-resolution, and thus a smaller resultant image. The same process can be applied to the smaller resultant image. This process can be iterated or repeated multiple times to create a series of images decreasing in resolution. Such resultant images, in conjunction with the high resolution source image, can be visualized as a sort of a pyramid in which the high resolution source image is a base, and each resultant image, ordered from highest resolution to lowest, is stacked above a previous image.

There are many benefits of using the pyramid or a multi-scale image representation. For example, in many cases of image retrieval, especially in image viewing applications, a large, high resolution image will have far more pixels than a display on which this image is to be displayed. Therefore, for example, a viewing application may be forced to severely scale down this image by a process of pixel blurring and subsampling. If a pyramid representation is not in use, then the viewing application often has no choice but to perform that potentially computationally expensive blurring and subsampling process at runtime, resulting in an undesirable viewing latency or viewing application unresponsiveness. However, if a high resolution image is part of an image pyramid, then the viewing application may render one of many lower resolution layers that have been generated. This rendering may be performed with little or no perceptible delay, as this rendering is computationally inexpensive. In cases of image analysis and processing, a pyramid representation provides a similar benefit. For example, where an application tasked with processing an image may need to analyze the image at a low resolution, if a low resolution layer is already present in a pyramid representation, then minimum or no potentially costly or time consuming blurring or subsampling need occur before the application can proceed to analyze the low resolution representation of the image.

A concern of non-pyramidal image representation or representing an image at only its highest resolution may be a direct result of a size of the high resolution image. For example, a high resolution image can contain require upwards of several gigabytes of information. A computational expense of blurring and subsampling is not a sole hurdle for viewing and processing applications. Transferring an entire high resolution image from one location on a disk or network to another can be prohibitively expensive, both in terms of time and bandwidth. A pyramid representation allows for far faster and more efficient transfer of information from storage—networked or local—to memory for use by the application. Because image pyramids are an efficient way to represent high resolution images, the image pyramids have relevance at least in a field of medical imaging, in which high resolution images may be ubiquitous.

WSI images, such as contained in files, are high resolution (on an order of from about one to about ten gigapixels or from about one to about ten billion pixels) digital images generated by special scanners which capture stained biological specimens on glass microscopy slides. Slide scanners output WSI files in a variety of formats, and each file can range in size from a few megabytes to dozens of gigabytes, depending on an image resolution and a compression scheme, if any. Accordingly, due to such size and structure, the files generated by the slide scanners are not optimal for viewing in a web browser over a network connection. Therefore, using a file or function library, such as an open-source Openslide library, the computing system 108 can process and convert WSI images of a variety of formats into a tiled, pyramid format known, as Deep Zoom Image (DZI). Note such tiling/tessellation can refer to a fact that most or every resolution layer of a pyramid is broken into potentially many small, square or other closed-shaped tiles, each a separate image file. Breaking each resolution layer into such tiles allows specific regions of an image to be accessed quickly and efficiently. For example, a WSI image converted into a DZI format file can yield an extensible markup language (XML) file with information about one or more dimensions of the WSI image, along with several directories, one for each resolution layer, containing most or all tiles that comprise a respective layer. A number of tiles per resolution layer can increases by a factor, such as four, from a given layer to a higher resolution neighbor. For example, a WSI image that is one gigabyte in size, when converted to a DZI format, may yield as many as from about 50,000 to about 100,000 total tile files across most or all resolution layers.

FIG. 6A shows a schematic diagram of a system to convert an image according to the present disclosure. The computing system 108 can convert an image, such as into a pyramid format, in many ways. As shown, the computing system 108 can employ a DZI process 600A, which involves a database 602A, which stores a plurality of images, and a DZI converter 604A, which can be a logic, such as a program running on a computing device, such as the server 110. Note that the database 602A can be a database using a relational or document-based data model. The database 602A may store image files or references to image files stored on separate storage devices, storage services, or file servers. The database 602A may also store associated metadata with image files or image file references. The database 602A may run on a respective computing device, connected to other system components via a physical or a network connection. Alternatively, the database 602A may share a computing device (hardware) with other system components.

Given a high resolution medical image, the computing system 108 converts such image into an image pyramid in a DZI format, or similar tiled or tessellated, pyramidal format. This conversion can be completed using a single or a combination of software tools, such as a VIPS application/library or an Openslide application/library. This conversion process results in a directory tree or other hierarchical structure containing image information (DZI Pyramid) and a file containing metadata, often, but not necessarily, represented in an XML format (Metadata). Both the directory tree and metadata file are written to the database 602A for storage. Note that the database 602 can be distributed or cloud-based, such as via a scalable, cloud-based platform, such as Amazon Web Services (AWS) Simple Storage Service (S3), which can be used as a service on which to store one or more WSI images because a single slide scanner is capable of generating upwards of 1 terabyte of data per day, which is an amount of data that could easily overwhelm a local storage system. However, a high number of individual files that comprise an image in DZI format can pose various storage issues when the image in the DZI format is to be stored on a cloud-based storage platform, such as S3. For example, many cloud-based storage platforms charge users for an amount of data the users store and transfer as well as a number of API requests the users make when storing or accessing data. For example, a PUT request can be used to upload a file to S3. To upload a WSI image in DZI format to S3 thus requires one PUT request for each individual tile, and one PUT request for the XML file containing metadata. As stated previously, a one gigabyte WSI image in DZI format could have roughly about 100,000 tiles, entailing over 100,000 PUT requests to upload in entirety. Since the cloud-based storage platforms charges users $X/Y PUT requests, a cost, then, to upload such WSI image to can be roughly $Z, which may surpasses a cost to cloud store such image for one year. This cost can be prohibitively expensive, and could prevent providers of the cloud-based storage platforms from being effectively used to store high resolution images in the DZI format. A practice for uploading several related files to a server can involve for the files to first be archived into one file, such as a TAR file or a ZIP file. The archive file can then be transmitted to a server in one request, and then the archive file can be expanded or un-archived into constituent files upon successful receipt by the server. However, cloud-based storage platforms do not support direct code execution, such as a code required to expand the archive file. Therefore, the archive file uploaded to a cloud-based storage platform may not be expanded in place. Further, note that simply archiving the DZI tiles will not effectively alleviate such drawback. Accordingly, concerns, such as prohibitively high costs of uploading WSI images in DZI formats to cloud-based storage platforms, such as S3, can be effectively alleviated when a solution minimizes a number of HTTP requests required to complete an upload process, while still preserving an integrity of one or more individual image tiles such that the individual image tiles can be accessed on-demand and as efficiently as independent or un-archived image tiles in the DZI format.

FIG. 6B shows a schematic diagram of a system to convert an image according to the present disclosure. The computing system 108 can convert an image, such as into a pyramid format, in many ways. As shown, the computing system 108 can employ a Aggregated DZI (ADZI) process 600B, which involves a database 602B, which stores a plurality of images, and a DZI converter 604B, which can be a logic, such as a program running on a computing device, such as the server 110, and an ADZI converter 606, which can be a logic, such as a program running on a computing device, such as the server 110. Note that the database 602B can be a database using a relational or document-based data model. The database 602B may store image files or references to image files stored on separate storage devices, storage services, or file servers. The database 602B may also store associated metadata with image files or image file references. The database 602B may run on a respective computing device, connected to other system components via a physical or a network connection. Alternatively, the database 602B may share a computing device (hardware) with other system components.

Given a directory tree and a metadata file outputted during a DZI process, the ADZI converter 606 begins a process of creating an archive file containing image data of most or all tiles in a newly created pyramid. The ADZI converter 606 initially creates an empty archive file and an empty map file. Then, the ADZI converter 606 traverses through a file system directory tree containing most or all resolution layer directories and respective constituent image tiles. For each image tile file, the ADZI converter 606 inputs the image data from that file and appends that file to the archive file. The ADZI converter 606 also tracks a resolution level and a two-dimensional (x,y) position of a respective tile. The ADZI converter 606 records in the map file an offset in bytes in the archive file at which the image data was written, as well as a length in bytes of the image data. The ADZI converter 606 then moves onto a next image tile file in order to iterate. At a conclusion of this archival process, the archive file is filled with concatenated image data from most or all tiles from all resolution layers, and the map file is filled with the byte offsets and lengths of each image tile, indexed by a resolution layer, an X-dimensional position, and a Y-dimensional position. The archive file and map file accompany the metadata file from the original DZI representation, leaving a total of three files which are written to the database 602B for storage.

Figure 7:
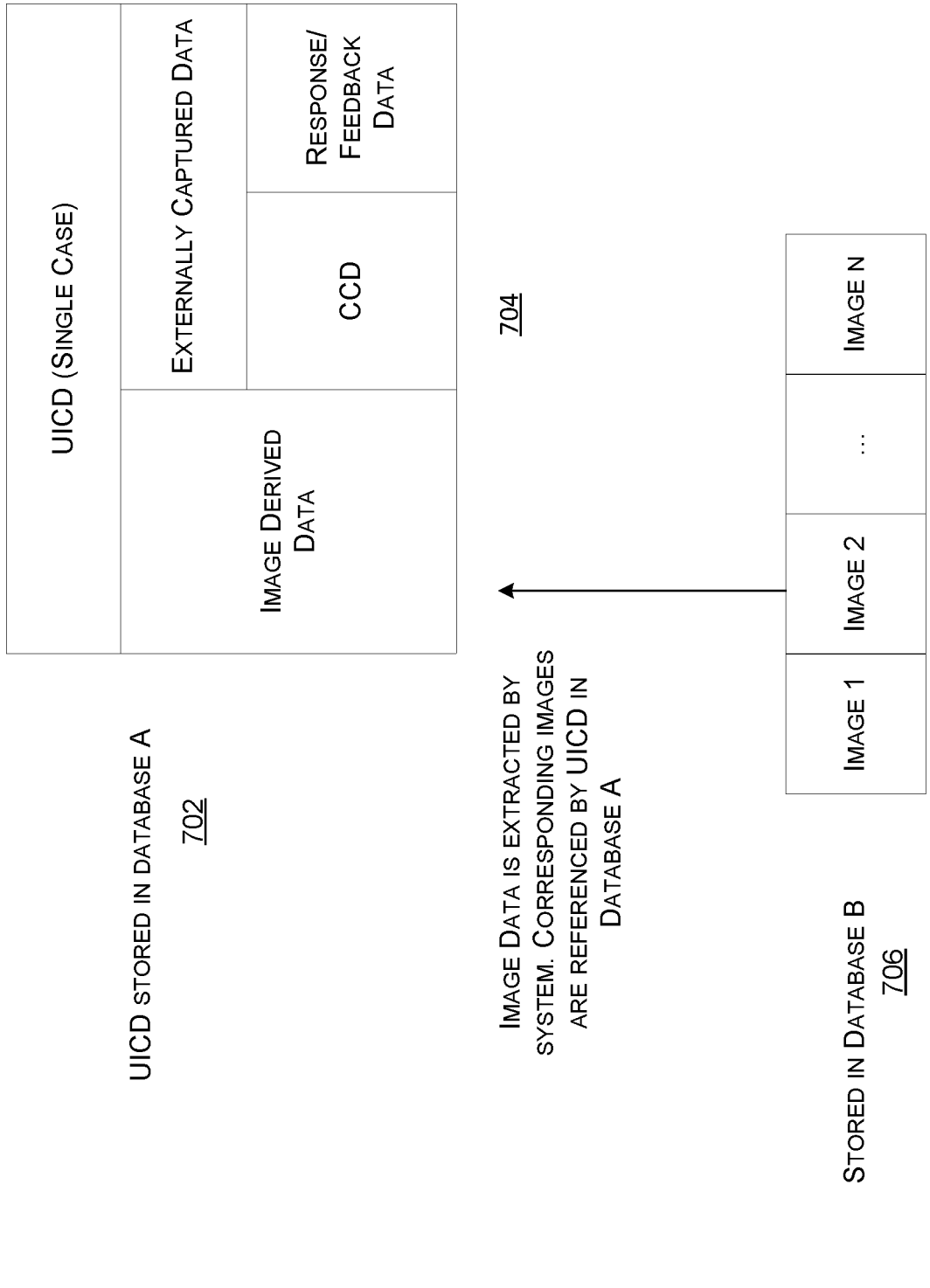
FIG. 7 shows a schematic of data organization according to the present disclosure.

FIG. 7 shows a schematic of data organization according to the present disclosure. As disclosed herein, one of many advantages of the computing system 108 is an ability to gather otherwise siloed or isolated data via a deployment in a networked environment, whether public or private or any combination thereof. Often, a shortcoming regarding a digital biopsy image or a data analysis, especially when involving machine learning or other sophisticated data analysis, may be in a limited scope of methods used to acquire such data. The computing system 108 is designed or includes a functionality, such as via a logic, to optimize data analysis of many samples collected over extended periods of time. The UICD is a case-specific aggregation of most or all data calculated and collected by the computing system 108, such as on a per patient basis or a group of patients basis. The UICD allows for effective filtering based on specific search criteria, and may serve as a fundamental unit of data for storage and analysis.

A database 702 stores one or more UICD records 704 using a relational or document-based data model. However, other database models or schemas are possible. The database 702 may run on a respective or dedicated computing device, connected to other system components via a physical or a network connection. Alternatively, the database 702 may share a computing device (hardware) with other system components. As shown in FIG. 7, the database 702 can comprise database A.

The UICD record 704 may include image-derived data, externally-captured data, contextual case data (CCD), and response/feedback data. The UICD record 704 may include user account information, computed image features, pathology report data, electronic medical record (EMR) data, references to other pieces of information within the computing system 108, tracking information, or user-supplied data. Note that a case refers to a medical or biological case, an instance in which a human, marine, aerial, animal, or other biological entity or subject has or is suspected of disease or any health abnormality, or is taking part scientific study or research of any type for any use where medical or biological information is desired. For example, a patient who is at risk for a cancer might undergo a screening for the cancer and the medical information that is gathered, including medical histories, would comprise a medical case. For example, a medical case can include many types of information about a patient or subject, recorded at one time, or over a period of time. Thus, such case may include or refer to many images. The UICD record 704 can be associated with one or more images and can contain both information about (a) the image(s), (b) the case as a whole, or (c) user interaction with the system in regards to that case or the images which comprise that case. The UICD record 704 may include information which may be real numbers, boolean values, alphanumeric or symbolic or character strings, and such information may be arranged, structured, or stored in a variety of formats, including, but not limited to scalars, vectors, matrices, trees, and key-value stores. Methods for extracting image derived data and methods for collecting externally captured data are further described herein.

One of many purposes or benefits of the computing system 108 is to enable an analysis of pathology images or related case data. While an image-derived component of the UICD record 704 provides a mathematical or representative currency for describing histological images, additional information may be present for many kinds of analyses. For example, there may be value to analyze correlations between image features extracted by the computing system 108 and historical case data associated with such images. Thus, the computing system 108 entails non-image data to be captured externally as part of one or more UICD records 704. There may be several overarching classes of externally captured data that can pass through or be generated by the computing system 108.

The CCD comprises data that is partially or completely independent of an initial image processing process that is performed by the computing system 108. One of many characteristics of the CCD within one of many contexts of the computing system 108 is that the CCD may not necessarily mandate corresponding images to be within the computing system 108. The CCD may be user-inputted or supplied by an external, automated, or semi-automated system. Other sources of the CCD may include, but are not limited to, pathologist reports, EMR, electronic health records (EHR), general case information, comments on cases, or medical histories. The CCD may enable for (a) providing additional input vector features for a case that enhances or allows predictive analysis during supervised or unsupervised learning phases, or (b) acting as an answer vector when training with a new set of data.

The response/feedback data comprises a class of information which refers to data gathered by the computing system 108 in response to an existing image input, or image processing by the computing system 108. For example, one of many distinguishing characteristics of the response/feedback data is that the response/feedback data involves an image to already have been passed or otherwise input into the computing system 108. For example, the response/feedback data may be considered in many situations to be feedback. Note that this class of information includes most or all data from recorded user interactions, such as via the clients 104, 106, within the computing system 108 interface, where such data may become associated with a single case and thus a UICD. For example, the response data may be gathered by recording mouse movements or other input device, such as a track pad or a touch pad, across a digital image or one or more tiles accessed by a user in a DZI viewer, such as a software application programmed to enable viewing of a DZI image. Such response data may be associated with a single image thereby becoming part of a UICD and may be leveraged in a UICD analysis for creating an automated region of interest identification algorithm. Other examples of the response data may include, but are not limited to, recordings of one or more user-inputted parameters for image analysis, one or more image analysis user-made adjustments, a user evaluation of an image analysis performance, a case-based or image-based application usage data, such as amount of time spent viewing an image, evaluating a case, or others, image annotations supplied by users, or tagging of images as belonging to a particular category or having certain attributes.

The computing system 108 is adaptive in that externally captured data can be used to enhance or adapt the computing system 108, notably, but not limited to an image analysis performed by the computing system 108. Frequently, some image analysis programs or algorithms involve some contextual data feedback for machine training of such programs or algorithms or for any defining, refining, or enhancement. Correlations between clinical data and image features can be great interest in machine-based pathology analysis programs or algorithms. Without the externally captured data, the computing system 108 may be difficult to adapt in order to account for variability within histology workflows. While some technologies for training machine-based histological image analysis and clinical diagnostics involve some sampling of the externally captured data, deploying one or more analysis programs or algorithms in the computing system 108 allows for significantly more dynamic data analysis, visibility into significantly greater ranges of pathology workflows, where statistical sampling can be far less biased.

The database 702 stores one or more UICD records 704, and thus includes information which may be real numbers, boolean values, alphanumeric or symbolic or character strings. The real numbers, boolean values, alphanumeric or symbolic or character strings may be arranged, structured, or stored in a variety of formats, including, but not limited to scalars, vectors, matrices, trees, and key-value stores. The database 702 stores information associated with one or more corresponding images, which are stored in a database 706. The database 706 can store data using a relational or document-based data model. However, other database models or schemas are possible. The database 706 may run on a respective or dedicated computing device, connected to other system components via a physical or a network connection. Alternatively, the database 706 may share a computing device (hardware) with other system components. As shown in FIG. 7, the database 706 can comprise database B.

Figure 8:
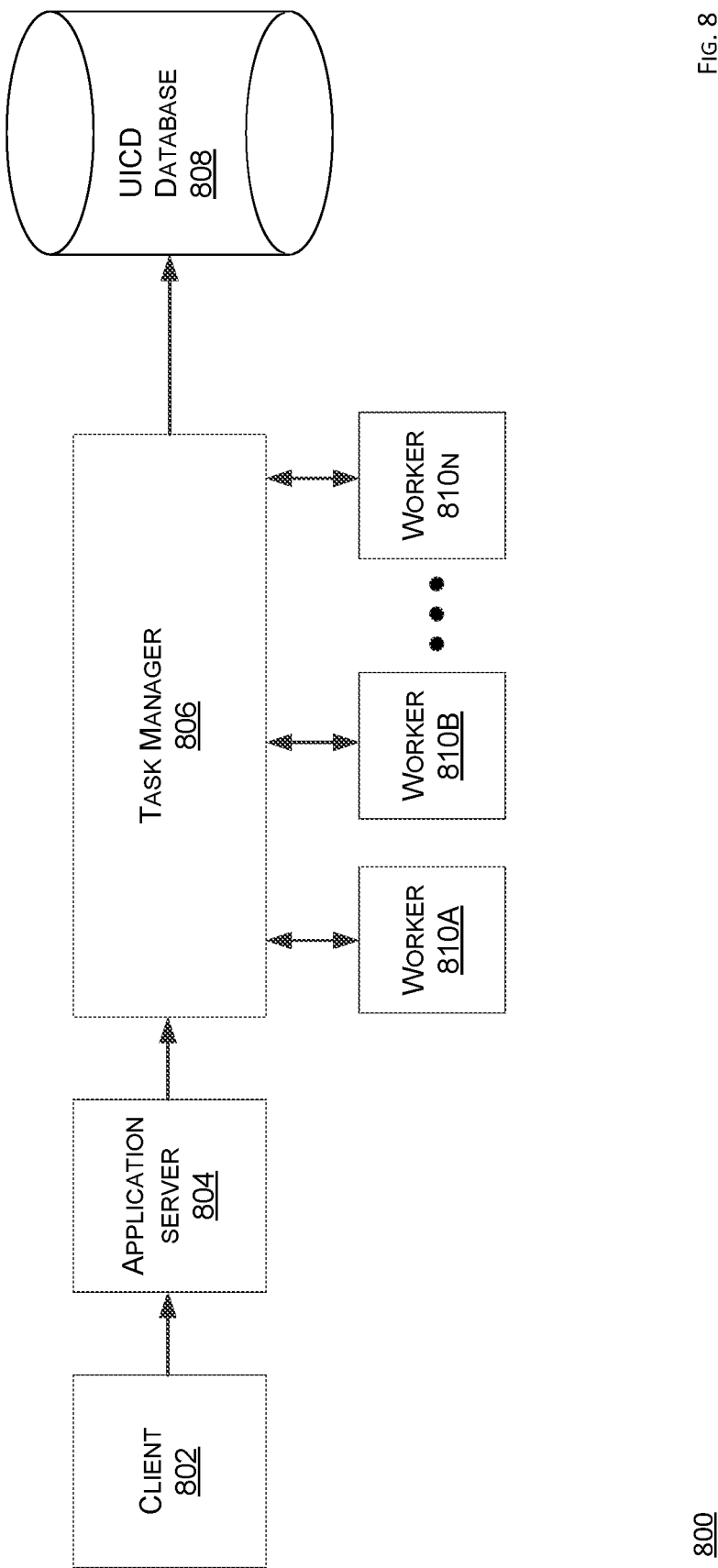
FIG. 8 shows a schematic view of an analysis topology according to the present disclosure.
Figures 9A, 9B, 9C:
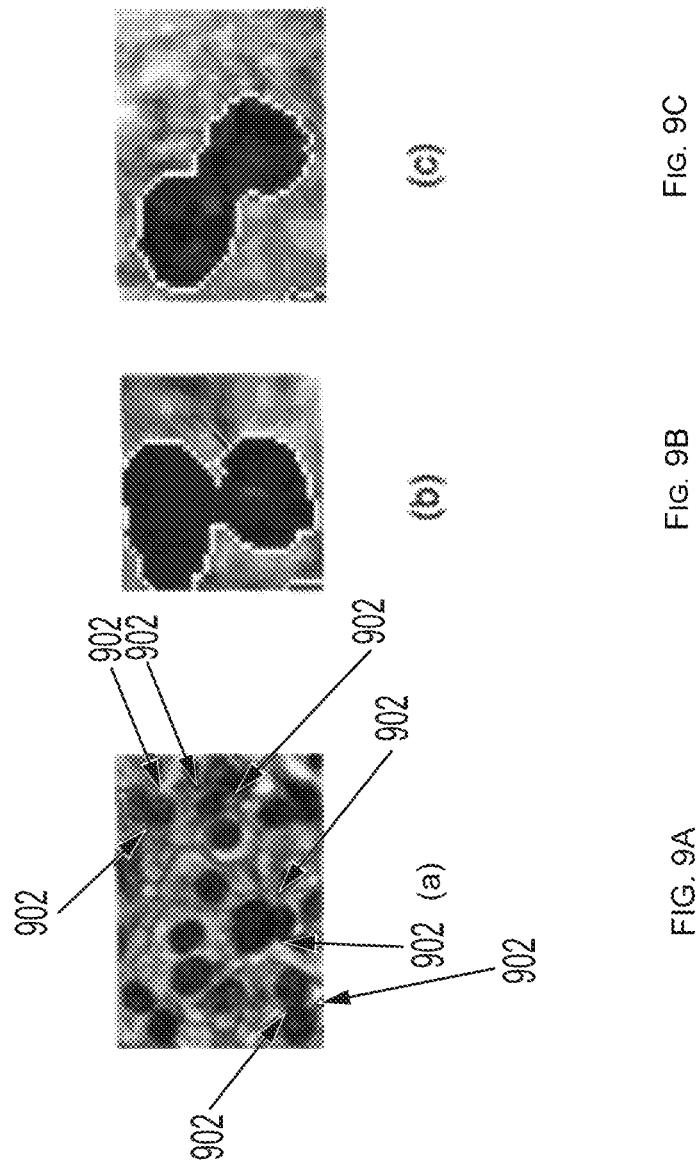
FIGS. 9A-9C show a plurality of images which can be used via a computing system disclosed herein according to the present disclosure.

FIG. 8 shows a schematic view of an analysis topology according to the present disclosure. FIGS. 9A-9C show a plurality of images which can be used via a computing system disclosed herein according to the present disclosure. An analysis topology 800 comprises a client 802, an application server 804, a task manager 806, a database 808, and a plurality of workers 810*a-n*. Note that any number of workers 810*a-n* can be used. The topology 800 involves one or more images, where one of such images can comprise a digital image represented in one of a variety of formats, such as .tif, .jpeg, .jpg, .svs, .vms, .vmu, .npdi, .scn, .mrxs, .tiff, .svslide, and .bif. However, note that such image can additionally or alternatively comprise a section of a DZI image or an ADZI image. The source of such image can be a database, such as the database 706.

At least one of the workers 810*a-n* can comprise a logic, such as a set of computer instructions, such as code, which may be executed as a separate thread in a task manager 806 process, or as a separate process executing on a same computer on which the task manager 806 process executes, or as a process on a computer distinct from that on which the task manager 806 process executes. At least one of the workers 810*a-n* is created at a command of the task manager 806, which specifies a set of computer instructions, such as code, which at least one of the workers 810a-n will execute. At least one of the workers 810a-n receives a digital image as an input from the task manager 806. During a course of, or at a completion of executing the set of computer instructions, at least one of the workers 810a-n outputs the image-derived data to the task manager 806.

For example, the set of computer instructions which at least one of the workers 810a-n will execute can comprise information describing one or more governing dynamics of one or more actions taken by the task manager 806 and one or more of worker 810a-n processes. Such instructions account for some modalities of modification of the image and are included but not limited to source code written in any language which provides an instruction for one or more of the workers 810a-n to modify a bitmap of the image or a portion of the bitmap of the image, or identify certain pixel classes or patterns that may represent one or more objects of interest within the image which will be a basis of feature extraction, whether such interest is predetermine, preselected or determined before, during, or after image processing. Also, such instructions for feature extraction are disclosed herein and include a modification and identification of most or any part of the bitmap of the image. A result of such instructions, and therefore, one or more features that the task manager 806 and a constituent worker process can create, comprises or defines the image-derived data.

A set of instructions to input the image can be formatted in a modular manner such that many specific steps instructed within such set of instructions may run in parallel or sequentially, independent of one another, such that one or more tasks of the specific steps can be allocated by the task manager 806 to one or more processes associated with the workers 810a-n in some manner that either splits a single task up among multiple worker 810a-n processes or runs multiple different tasks simultaneously amongst multiple worker 810a-n processes. This splitting or segmentation of the instructions creates two or more subsets of instructions that act as the input instructions in conjunction with the image. Once at least one of such scenarios coalesces to at least partial completion, then the task manager 806 aggregates one or more results as the image-derived data for reporting, recordation, and storage into the database 808.

A process of modifying and identifying one or more components of an image is a computationally expensive task. Therefore, to reduce runtime and increase throughput, the computing system 108 utilizes a logic, such as a component program, a function, a routine, a class, an object, or a set of computer instructions, functioning as the task manager 806. The task manager 806 divides or allocates work among several independent worker 810a-n processes, such as instructions, functions, or programs which may be each assigned a whole image or a region of the image on which to carry out some subset of the instructions or operations. The task manager 806 dispatches the workers 810a-n and listens for one or more messages from the workers 810a-n. Such messages, if any, may contain information on task progress and output, may be collected, organized, or amassed into a queue and read sequentially by the task manager 806. For example, one or more progress messages may be relayed to a user-facing console or graphical user interface page to provide the user with an expected time of task completion. Data from messages containing process output (quantification results) may be parsed and marshaled into a data structure containing output from most or all the independent worker 810a-n processes. Independent worker 810a-n processes may complete tasks in arbitrary order, though the task manager 806 tracks a completion status of each of the workers 810a-n. When most or all of the workers 810a-n are in a completed state does the task manager 806 pass an aggregated image-derived data output to a next component, such as the database 808.

One of many purposes of the computing system 108 is to process and analyze a digital tissue scan image. Therefore, there may be a desire or an interest to extract information about such image as a whole (image content or image metadata) or about one or more objects within such image (image object), such as counting a number or size of one or more nuclei represented in such image. A unit of information about such image or an image object comprises an image feature. One or more image features are computable and such computation may involve one or more specialized image processing algorithms whose functionality is described by one or more sets of instructions, as disclosed herein. For example, the specialized algorithms may include but are not limited to image segmentation, noise reduction, image transformations, and measurements of the image or any constituent objects (where objects comprise groups of one or more image pixels). As disclosed herein, one or more image features, combined with other information in the task manager 806, and performed by a same or possibly other worker 810a-n processes are collected, organized, or aggregated in the task manager 806 and may form a UICD, such as the UICD 704. Note that such image features may be numerical or mathematical. Image features may be real numbers, boolean values, alphanumeric or symbolic or character strings, and they may be arranged, structured, or stored in a variety of formats, including, but not limited to scalars, vectors, matrices, trees, and key-value stores. The image feature extraction process involves processors or processing/computing power. As in a format conversion process disclosed herein, the computations are provided via the workers 810a-n.

Image metadata comprises contextual information about an image, i.e., information about a creation of the image or information that can aid in image interpretation. Metadata may be dependent on file type and a scanning method used to create a digital biopsy image. Examples of image metadata include, but are not limited to file type, file size (bits), scanner used, device model, device version, microns per pixel, illumination source, objective power, physical width, physical height, x-offset from scanner, y-offset from scanner, focus offset, bits per pixel, pixel order, x-resolution, y-resolution, or others.

The task manager 806 may allocate worker 810a-n processes to aggregate metadata from an image, if one or more instructions provided with an input command, instruct the task manager 806 to handle the image metadata either immediately after accepting such metadata from a user, or the task manager 806 may defer metadata extraction to a later time, if and when a need for such metadata arises. Note that the task manager 806 can be embodied in logic, whether hardware or software.

Performing computational tasks on an image can occur at several time points from a perspective of a user controlling the computing system 108. For example, one time point is immediately upon transfer of the image into the computing system 108. Processing during this time may or may not be explicitly designated by the user during or before transfer. For example, the computing system 108 may, but is not required to, prompt the user whether or not certain computational tasks should be performed automatically upon transfer into the computing system 108. Another time point is during which an image may be processed after the image is already in storage, such as the database 706. Thus, upon an initial transfer of the image into the computing system 108, a request handler may determine whether the image should be fed into one of many processing paths, such as path A AND path B, or ONLY path B. Note that a possibility exists that the image passes only through path A, but that would only occur if the user did not request storage of the image or a viewable format of the image, such as a DZI format.

The computing system 108 can implement a computational method for quantification of biopsied tissue samples. This method may work in at least partial generality. For example, a listing of quantitative features, such as metrics, quantitative metrics, or tissue metrics, can enable a provision of less subjective analysis of slides and allow slides to be evaluated faster or more efficiently. Moreover, various computer vision methods can be used for computationally segmenting important tissue elements in a fast manner, while other or same methods can extract quantitative metrics given a position and a shape of such elements, such as objects, within a tissue image. Note that the quantitative features or the metrics may include abstract measurements or representations of an image as in-image transforms or an output of an image generated by convolving or performing some operation on that image with a filter.

A diverse, comprehensive, and accurate list of computed tissue features is important for various reasons. For example, one of such reasons is for human review/analysis of one, some, or all quantitative metrics as being indicative of biological phenomena, chemical presence, disease presence, disease state, biopsy or tissue quality, or stain quality, or might act in assisting workflow by helping to identify regions of interest. For example, another one of such reasons is for data analysis that may use such features to provide explicit, computationally evaluated estimates or predictions of medical conditions or biological phenomena that include but are not limited to, chemical presence, disease presence, disease state, slide quality, biopsy or tissue quality, or stain quality, or suggested regions of interest.

The client 802 sends information to the application server 804 via a request which may contain or reference an image. A type, size, or format of the image can be of any type. For example, the image may depict human, animal, marine, aerial, or other biological tissue. Note that this tissue is excised and stained with antigens which adhere to certain structures within the tissue for illumination and quick discernment for a human eye or a computer-based system to identify and measure various features about such structures. Some of the stains used include but are not limited to Hematoxylin and Eosin (a staining technique that uses Hemotoxylin and Eosin agents to highlight nuclei blue-violet or brown and other tissue light to dark pink), Feulgen (a staining agent and technique which depends on an acid hydrolysis of deoxyribonucleic acid (DNA) to identify chromosomal material or DNA in cell specimens), Fluorescent In Situ Hybridization (a technique that uses fluorescent probes to identify certain cells, nuclei or other histological objects of interest), Immunohistochemical (a practice of staining tissue with antigens or antibodies that can illuminate certain cells, nuclei or other histological objects of interest) or any other staining agent the allows nuclei, DNA, chromosomal material, and/or cell membranes within such tissue to be visually identifiable by human or computational methodology either before or after mathematical image transforms. The image may be, but is not limited to a WSI image or a static tissue image. The image may be produced by any device such as, but not limited to a slide scanner, microscope camera attachment, or microscopes with built-in or integrated cameras. Note that multiple images of a same specimen may be stitched together by computational methods before analysis via the computing system 108, as disclosed herein. For example, file formats may include but are not limited to at least one of .tif, .jpeg, .jpg, .svs, .vms, .vmu, .npdi, .scn, .mrxs, .tiff, .svslide, .bif, or .dzi. The tissue may excised from the human or animal via surgical biopsy, fine needle aspiration, or any other technique that allows for tissue sections that can be fixed on a glass slide.

The computing system 108 can comprise or run a computer program or a part thereof. This program might run on any computing environment, such as but not limited to single desktop or laptop computer, any mobile device, a single server, or a computing cluster.

A quantitative analysis process entails calculating numerous metrics, which comprise an output signal that are sent to a database, such as the database 808, upon calculation. Such metrics fall into categories including, but not limited to general (non-parameterized) image metrics, object morphometry metrics, and tissue architecture metrics. The metrics that are created from the output signal are a product of the set of instructions being performed on the image as distributed to one or more worker 810*a-n* processes by the task manager 806.

General, non-parameterized image metrics, such as features, may be useful because such metrics may capture a great deal of information about the image without being tethered to a particular domain, such as tissue or cancer type, and without requiring specialized tuning or supervision. Although correlations between subsets of such metrics and prognostic data may not seem intuitive, published research has shown that such correlations not only exist, but are also highly effective at predicting prognostic outcomes. General, non-parameterized image metrics may also be segmentation-independent and modify the input image in accordance with the set of instructions.

General, non-parameterized metrics, such as features, may be calculated by computing on an image space a number of mathematical transformations, such as Wavelet, Fast Fourier, Chebyshev, or others. Such metrics included from one or more image properties of such transformations include, but are not limited to, Radon features, edge statistics, object statistics, multi-scale histograms, tamura features, Gabor features, Chebyshev features, Zernike features, Chebyshev-Fourier features, or others.

In order to calculate morphometric features, the computing system 108 may perform a segmentation step, which illuminates one or more foreground objects of interest from a rest of a background noise contained within the image. Such objects which may be segmented include but are not limited to nuclei, lymphocytes, glands, tertiary lymphoid structures, epithelial regions, regions of high mitotic activity, and other histological objects or regions within an image that may be of interest. This task of segmentation can be performed when dealing with digital scans of Hematoxylin and Eosin stained biopsies, which may be stains on biopsies in pathology. Such segmentation process can be broken into or comprises a plurality of steps: (1) image preprocessing and de-noising, (2) intensity threshold-based edge/blob detection, (3) contour evaluation, and (4) cluster and overlap resolution. Note that such steps may be extensible, with room for parameter optimization within the computing system 108, for many of objects disclosed herein or others that may not be disclosed herein.

Segmenting one or more nuclei of a tissue image stained with Hematoxylin and Eosin can be performed during image pre-processing. The image undergoes contrast normalization to account for a variability inherent in handling images from a variety of different tissue scanners. Then, the computing system 108 may choose to de-convolute an input three channel red-green-blue (RGB) image into a plurality of separate single channel images-one for hematoxylin and one for eosin, which comprise the Hematoxylin and Eosin stain. This processing provides a desirable side-effect of highlighting the nuclei, which during slide treatment, are most affected by the hematoxylin staining agent. Additionally, the computing system 108 may apply one or more blurring filters, such as radial, Gaussian, or others, to the image in order to reduce noise. Noise reduction reduces the a of non-nuclear artifacts clouding or otherwise negatively affecting the intensity threshold-based edge/blob detection phase.

Next, the computing system 108 identifies or pinpoints edges and blobs in the image. Such edges and blobs are present where an intensity differential between pixels exceeds a particular value, which can be preset by a user. This value can either be empirically set, or determined dynamically by the computing system 108, such as via a heuristic. Dynamic determination by the computing system 108 can take advantage of a histological context where a relevant pixel is positioned. Specifically, a threshold value in a stromal region of tissue could differ from a threshold value in an epithelial region. Stromal and epithelial regions take on different colors when treated with an Hematoxylin and Eosin stain. Therefore, such regions may be treated differently in the edge and blob detection phase.

Next, the computing system 108 evaluates one or more results of the edge and blob detection phase to find or search for most or all closed contours. Closed contours that have an area significantly below a cutoff value for a nuclear area are discarded or ignored or deleted. This cutoff value can either be empirically set or derived from a mean nuclear area of a dataset extracted from a number of images similar to the image. One of many effects of this size-based filtering is to remove contours that do not correspond to nuclei from the contour set.

Next, the computing system 108 traces one or more filtered contours to locate one or more points of concavity, which are generally indicative of a contour which spans a cluster of multiple nuclei, rather than just one. Cluster contours may be frequent because nuclei may be clustered tightly in such a way that prevents the edge and blob detection from separating touching objects (objects which share a border). FIG. 9A shows a plurality of concavity points 902 on a number of different clusters.

Next, having marked a subset of most or all contours as cluster contours, the computing system 108 begins the cluster and overlap resolution phase, where each cluster contour is split or segmented into two or more contours representing a component nuclei. To accomplish this, the computing system 108 may employ an active-contour strategy similar to that proposed by Ali, Sahirzeeshan, et al. "Adaptive energy selective active contour with shape priors for nuclear segmentation and gleason grading of prostate cancer." Medical Image Computing and Computer-Assisted Intervention-MICCAI 2011. Springer Berlin Heidelberg, 2011. 661-669. Instead of using a "shape pior" model described by Ali, Sahirzeeshan, et al. "Adaptive energy selective active contour with shape priors for nuclear segmentation and gleason grading of prostate cancer." Medical Image Computing and Computer-Assisted Intervention—MICCAI 2011. Springer Berlin Heidelberg, 2011. 661-669. Ali, Sahirzeeshan, et al., the computing system 108 may instead use an ellipsoid as a bound for a contour evolution, or add a term to an evolving function to encourage a certain degree of roundness or eccentricity in a contour.

The segmentation process can be manageably split or segmented by the task manager 806, which would distribute to one or many worker 810*a*-*n* processes. Also, the segmentation process can be distributed such that each worker 910*a*-*n* process manages, controls, or commands a portion of the image at large and concatenates one or more arrays returned from object segmentation into a list of arrays containing one or more positional coordinates of the contours describing one or more boundaries of the objects.

An array of contours describing one or more segmented nuclei is used as a fundamental unit for calculating one or more morphometric features. Such contours describing one or more segmented histological objects are subject to quantification of metrics describing one or more properties of the contours and intensity values of one or more pixels within one or more boundaries of the contours.

The array of contours generated during the segmentation process may be combined with one or more instructions to one or many worker 810*a*-*n* processes. Then, a number of morphometric features may be calculated via the task manager 806 distribution to worker 810*a*-*n* processes. The morphometric features are calculated on an array of contours using a set of instructions for each single item or member or record in the array of contours. This information is aggregated via the task manager 806 and sent to the database 808 for storage.

Nuclear segmentation of a Hematoxylin and Eosin stained image, morphometry metrics can be calculated to capture information about a shape, texture, size of one or more nuclei in an image of a tissue. Significant chromosomal alterations indicative of a genetically unstable tissue, such as tumorous tissue, may be marked by an abnormal DNA content, which may manifests via in morphometric variations. Thus, nuclear morphometry features have clinical relevance as signals (predictors) of tumor aggression. Nuclear morphometry metrics include, but are not limited to: roundness: 1) how close a nucleus's shape is to that of a circle, 2) area: an area of a nucleus in terms of either pixels or microns, 3) perimeter: a perimeter of a nucleus in terms of either pixels or microns, 4) mean gray value: a mean intensity of pixels comprising a nuclear body, 5) maximum gray value: a maximum intensity of pixels comprising a nuclear body, 6) minimum gray value: a minimum intensity of pixels comprising a nuclear body, 7) skew gray value: a skewness of an intensity distribution of pixels comprising a nuclear body, 8) feret x: a width of a rectangular bounding box around a nucleus, 9) feret y: a height of a rectangular bounding box around a nucleus, 10) peak count: a number of instances where one of neighboring pixels has a gray value less than that of a currently evaluated pixel, and one of neighboring pixels has a gray value greater than that of a currently evaluated pixel, 11) valley count: a number of instances where both neighboring pixels have a gray value greater than that of a currently evaluated pixel, 12) slope count: a number of instances where both neighboring pixels have a gray value less than that of a currently evaluated pixel, 13) coarseness: a slope count−(2*peak count−valley count), 14) minimum diameter: a minimum diameter through nuclear centroid, 15) maximum diameter: a maximum diameter through nuclear centroid, 16) elongation: a ratio of maximum diameter to a minimum diameter, 17) summed optical density: a sum of individual intensity values of pixels comprising a nuclear body, 18) average optical density: a summed optical density divided by a number of pixels comprising a nuclear body, 19) minimum optical density: a minimum individual intensity value of a pixel in a nucleus, 20) maximum optical density: a maximum individual intensity value of a pixel in a nucleus, 21) a median optical density: a median individual intensity value of a pixel in a nucleus, 22) a standard deviation of optical density: a Measure a standard deviation of intensity distribution through individual pixels in a nucleus, 23) a skewness of optical density: a skewness of intensity distribution through individual pixels in a nucleus, 24) excess of optical density: a standard amount of intensity through individual pixels and an identification of a scalar difference between an actual optical density and a standard amount. This information may be aggregated and sent to the database 808 for storage.

In order to account for a variance of such metrics, which may be calculated for each nucleus detected across an image, some statistical features may be calculated as well in order to represent a distribution of one or more feature values across most or all objects detected within an image of a tissue. Such statistical distribution metrics include but are not limited to mean, variance, standard deviation, skewness, kurtosis, or others. This information is aggregated and sent to the database 808 for storage.

A spatial arrangement of nuclei and nuclear clusters are modeled using graphs constructed using individual nuclei, or clusters of nuclei as vertices. Features extracted from these graphs may have relevance to biology. Graphs, such as Voronoi, Delaunay, or others, capture global tissue architecture information, while specialized graphs focus on local groups of nuclei. Together, metrics extracted from such graphs provide dimensions with which to quantify and classify tissue. Examples of tissue architecture graph metrics include, but are not limited to: 1) giant connected component, 2) number of connected components, 3) average eccentricity, 4) percentage of isolated points, 5) number of central points, 6) skewness of edge lengths, 7) Voronoi cell area (mean, standard deviation, minimum, maximum), 8) Voronoi cell perimeter (mean, standard deviation, minimum, maximum), 9) Delaunay cell area (mean, standard deviation, minimum, maximum), and 10) Delaunay cell perimeter (mean, standard deviation, minimum, maximum). This information is aggregated and sent to the database 808 for storage.

One or more morphometric metrics calculated for nuclei of an image of a tissue may be extensible in a similar manner as the segmentation process is extensible. Many similar morphometric features and tissue architecture features can be calculated of any segmented object or region. For the tissue architecture procedure, one or more centroids of whatever region or object is being segmented is used as a vertex for a graph construction. The feature extraction process is extensible at least in part because one or more properties of one or more contour values and pixels within a boundary of one or more contours may be a point of interest for evaluating the tissue depicted in the image.

FIG. 10 shows a schematic view of a delivery topology according to the present disclosure. A delivery topology 1000 includes a client 1002, an application server 1004, and a database 1006, where the application server 1004 is communicably interposed between the client 1002 and the database 1006.

The client 1002 can comprise a program or an application running on a computer, such as desktop or mobile, either natively in a stand-alone application or through a web browser. The client 1002 enables a user to interact or interface with the application server 1004 to access content, including, but not limited to images stored in the database 1006, or case or image-derived data found in the database 1006. The client 1002 may contain a number of logic components, whether hardware or software, including but not limited to, an image viewer, a table of information, and an array of controls to interact with at least one of the components.

The application server 1004 can comprise a program or an application running on a desktop computer, dedicated server, or virtual machine running in a cloud-computing infrastructure. The application server 1004 acts as a bridge between the client 1002 and content stored in a database of the computing system 108, such as the database 1006. The application server 1004 may also couple or connect physically or over a network connection to the task manager 806.

The client 1002 communicates with the application server 1004 via a network connection, such as an intranet or Internet. The client 1002 may communicate with the application server 1004 via an HTTP protocol, with or without Transport Layer Security or Secure Sockets Layer (SSL). The client 1002 may communicate with the application server 1004 via another protocol, including, but not limited to FTP, Secure File Transfer Protocol (SFTP), or others. The client 1002 may communicate with the application server 1004 in an authenticated manner. Such authentication may be accomplished differently depending on a communication protocol used. For example, for the HTTP protocol, one or more authentication methods may include, but are not limited to a session cookie, OAuth, and/or authentication via a trusted third-party including, but not limited to a social networking service, such as LinkedIn, Google, Facebook, or others.

The client 1002 may request a file containing or referencing an image from the application server 1004. The application server 1004, upon receipt of such request, may verify that the client 1002 has permission to access the image, as requested. This verification may be accomplished by the application server 1004 checking that this request is authenticated, and that the image is listed as available to a user who authenticated the client 1002. In an event of a failed verification, then the application server 1004 may indicate to the client 1002 that an error has occurred, and the application server 1004 will not return the image, as requested. In an event that the request is verified, or that the request does not require verification, then the application server 1004 will query the database 1006 for the image, as requested. If such image is found in the database 1006, then the database 1006 sends the image to the application server 1004, which in turn sends the image to the client 1002. However, if such image cannot be found in the database 1006, then the application server 1004 may indicate to the client 1002 that the image, as requested, cannot be found. Upon receipt of the image from the application server, the client 1002 may display the image on a display associated with the client 1002.

Figure 11:
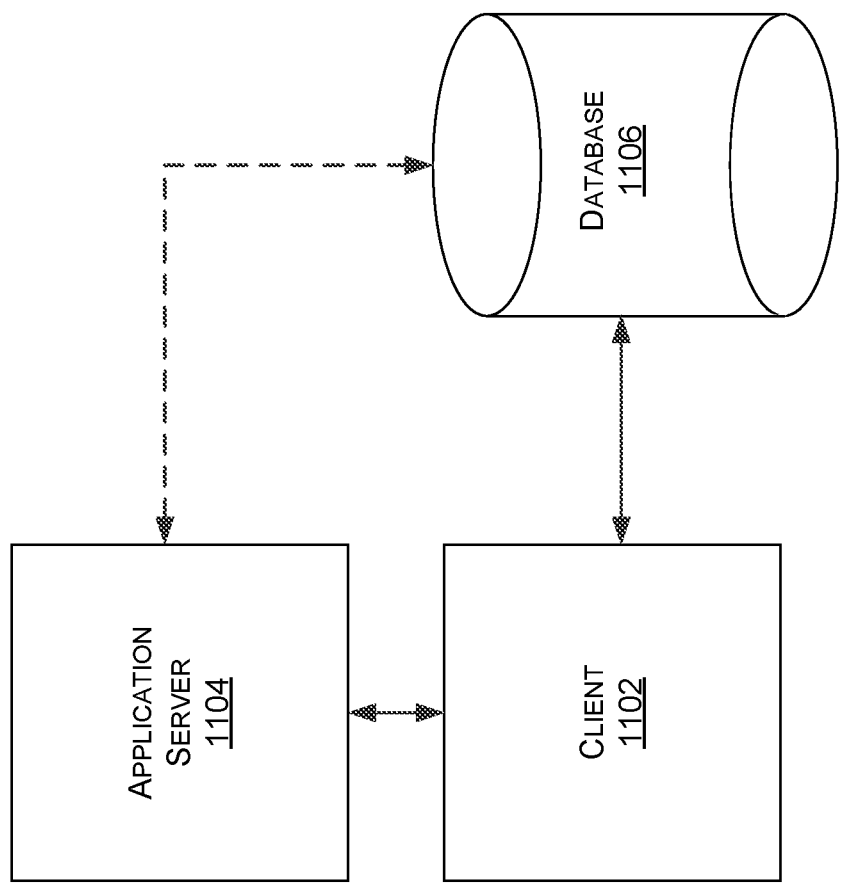
FIG. 11 shows a schematic view of a delivery topology according to the present disclosure.

FIG. 11 shows a schematic view of a delivery topology according to the present disclosure. A delivery topology 1100 includes a client 1102, an application server 1104, and a database 1106, where the client 1102 is communicably interposed between the application server 1104 and the database 1106. Optionally, the database 1106 may be coupled to the application server 1104.

The delivery topology 1100 differs from the delivery topology 1000 in a workflow architecture. Instead of requesting an entire image file from the application server 1104, the client 1102, per an ADZI process, as disclosed herein, may place a plurality of requests to the application server 1104 for small regions, or tiles, of a larger image file.

The process of making such requests for small regions, or tiles of a larger image file comprises streaming. For example, as per the ADZI process, the client 1102 first requests, from the application server 1104, a map file corresponding to an image that the client 1102 seeks to stream. Upon receipt of the map file from the application server 1104, the client 1102 can parse the map file to ascertain a total number of tiles the client 1102 can stream, along with information desired to access each tile, specifically, a length in bytes of a respective tile, and an offset in bytes of the tile in image's ADZI archive file stored in the database 1106. With such information, the client 1102 can directly connect to or directly interface with the database 1106, and request a correct number of bytes from a correct location in the database 1106 in order to receive a data of at least one tile. The client 1102 may perform several tile requests in parallel, or in rapid sequence to provide a smooth, responsive, and bandwidth-efficient image viewing experience for a user.

The client 1102 may request data from one or more UICD records via the application server 1104. The application server 1104, upon receipt of a request from the client 1102, may verify that the client 1102 has permission to access the one or more UICD records. This verification is accomplished by the application server 1104 checking that the request from the client 1102 is authenticated, and that the one or more UICD records is listed as available to a user who authenticated the client 1102. In an event of a failed verification, the application server 1104 may indicate to the client 1102 that an error has occurred, and the application server 1104 will not return the one or more UICD records. However, in an event that the request is verified, or that the request does not require verification, the application server 1104 queries the database 1106 for the one or more UICD records. If the one or more UICD records is found in the database 1106, then the database 1106 sends a copy of the one or more UICD records to the application server 1106, which in turn sends a copy of the one or more UICD records to the client 1102. If the one or more UICD records cannot be found in the database 1106, then the application server 1104 may indicate to the client 1102 that the one or more UICD records cannot be found. Upon receipt of the one or more UICD records from the application server, the client 1102 may at least partially display the one or more UICD records a display associated with the client 1102.

Figure 12:
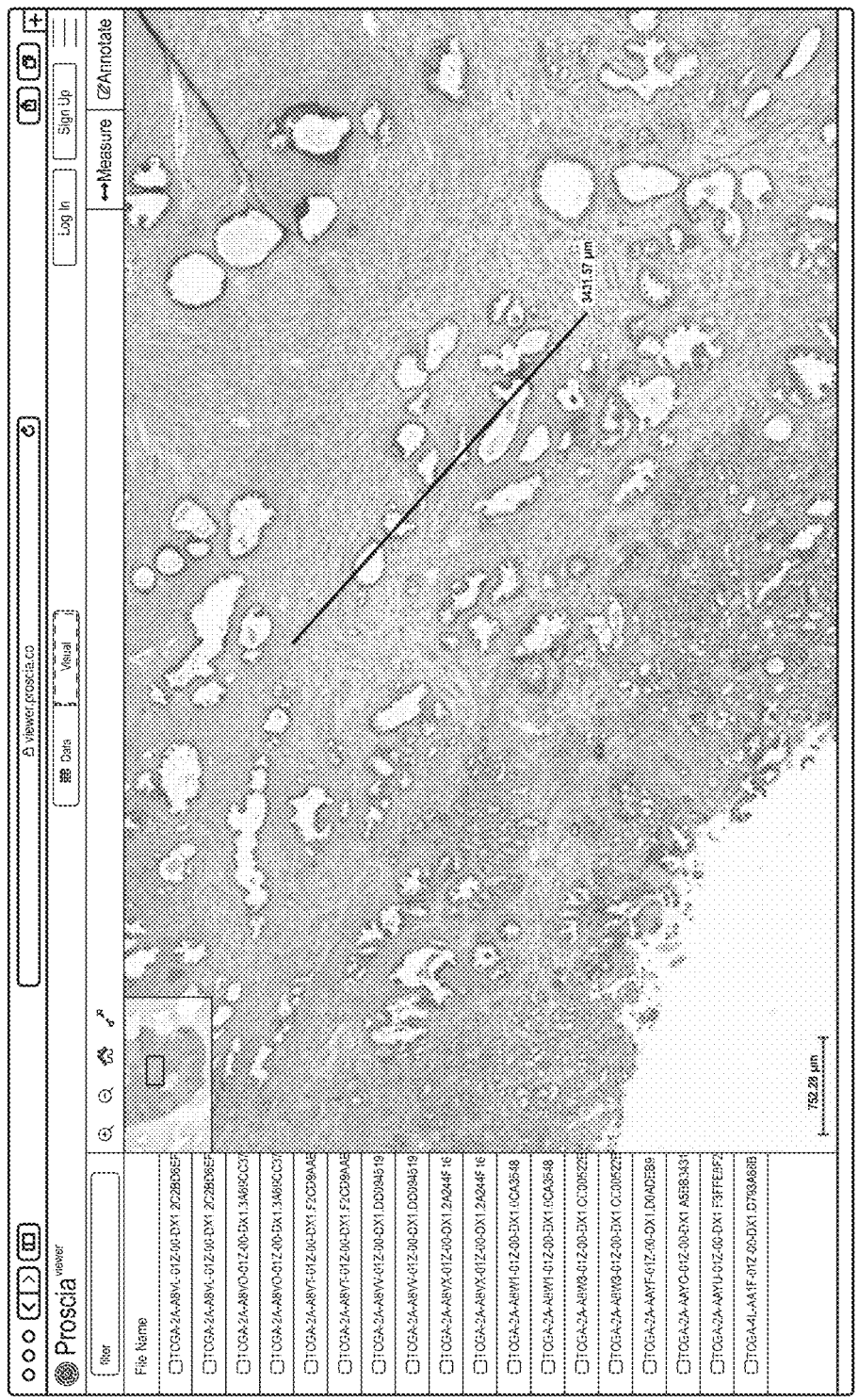
FIG. 12 shows an example embodiment of a user console comprising a measurement tool according to the present disclosure.
Figure 14:
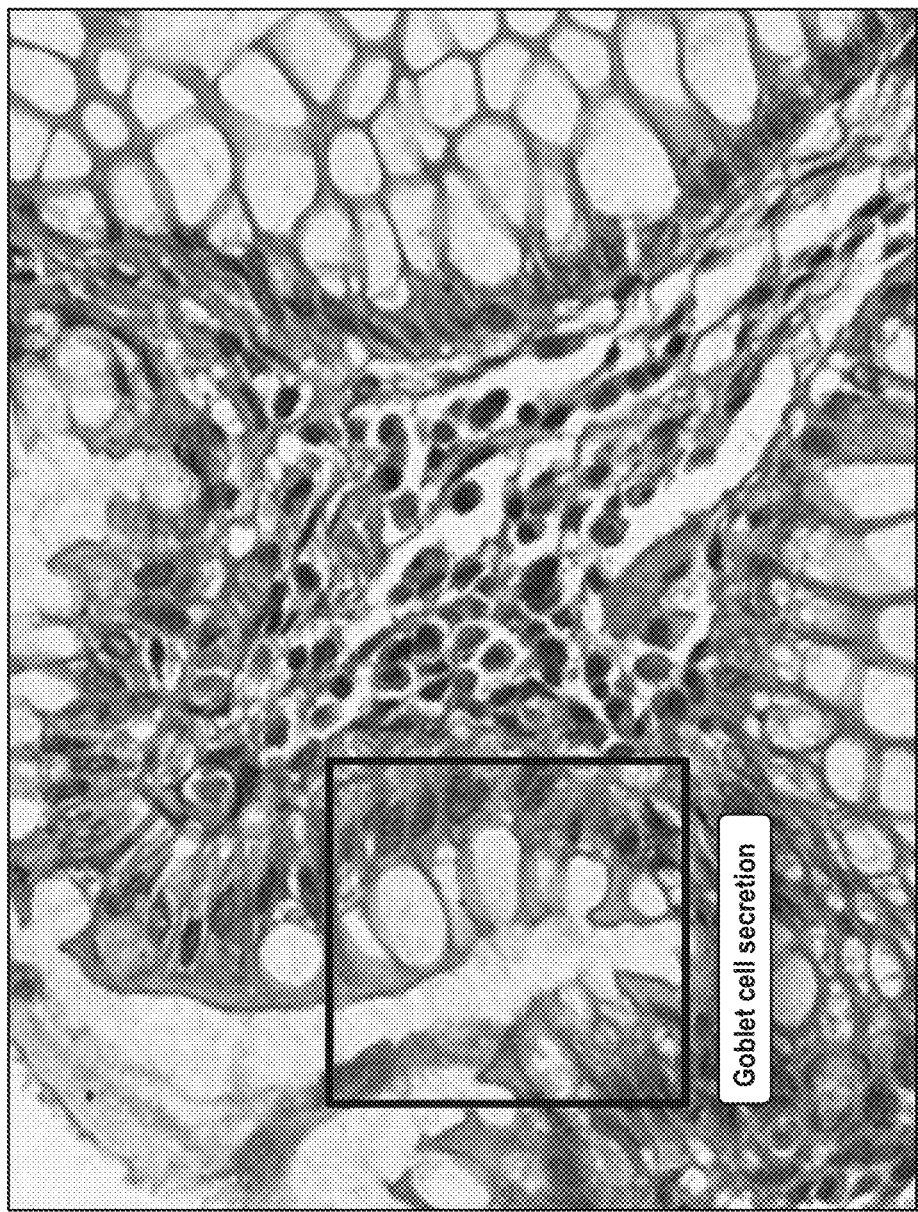
FIG. 14 shows an example embodiment of a user console comprising an annotation tool according to the present disclosure.
Figure 15:
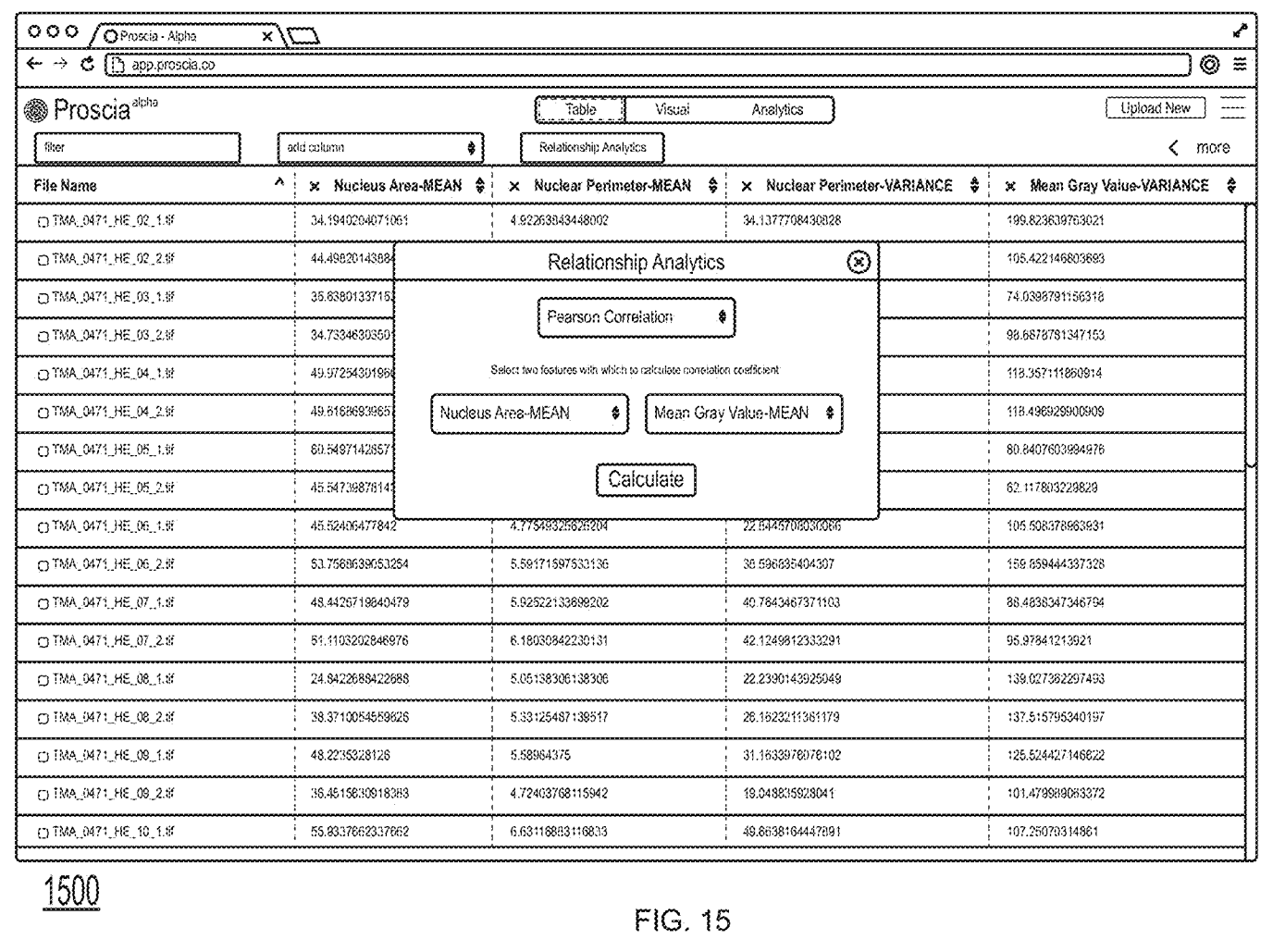
Figure 16A:
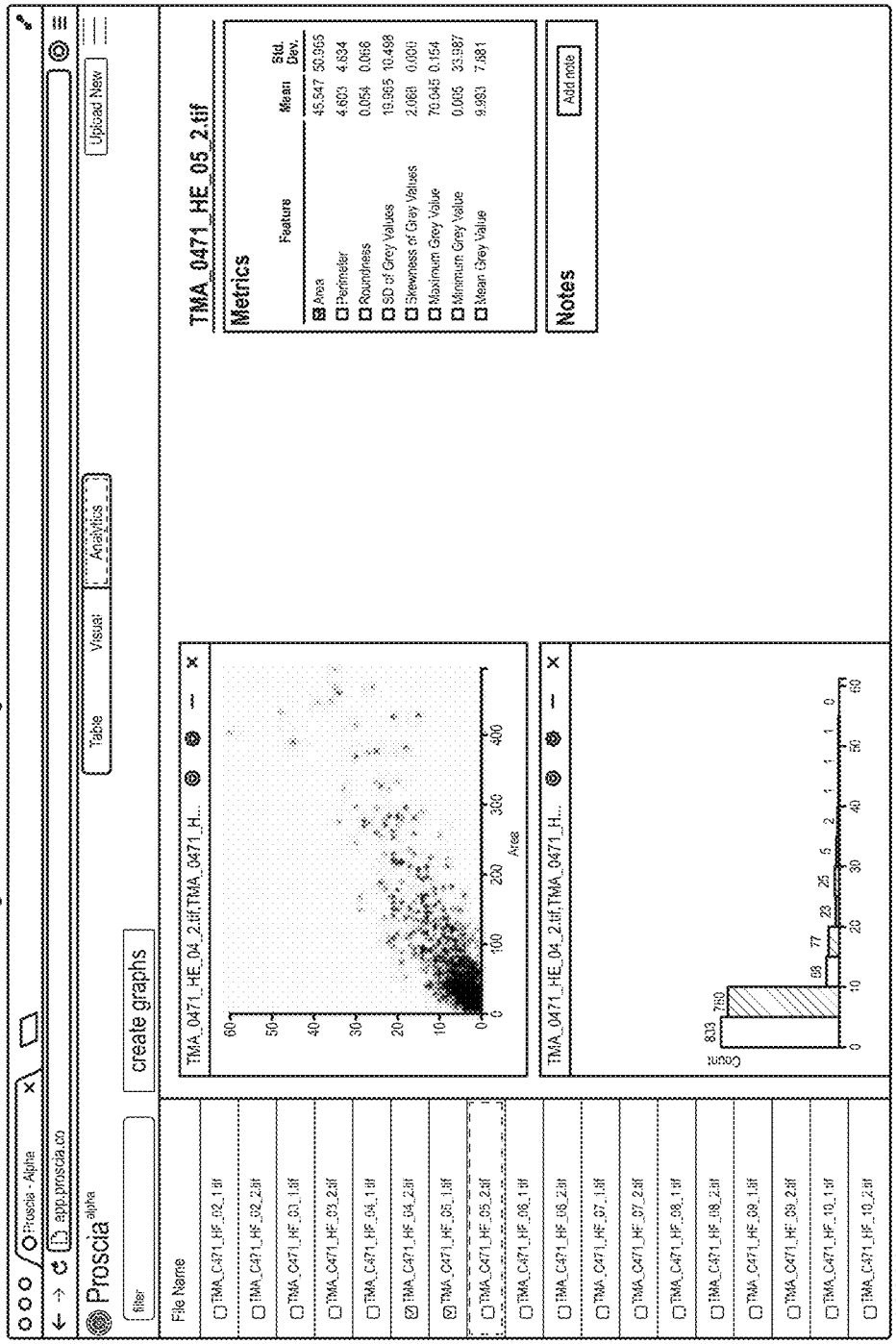
FIGS. 16A-16B show a plurality of example embodiments of a plurality of user consoles comprising a plurality of data visualization tools according to the present disclosure.
Figure 16B:
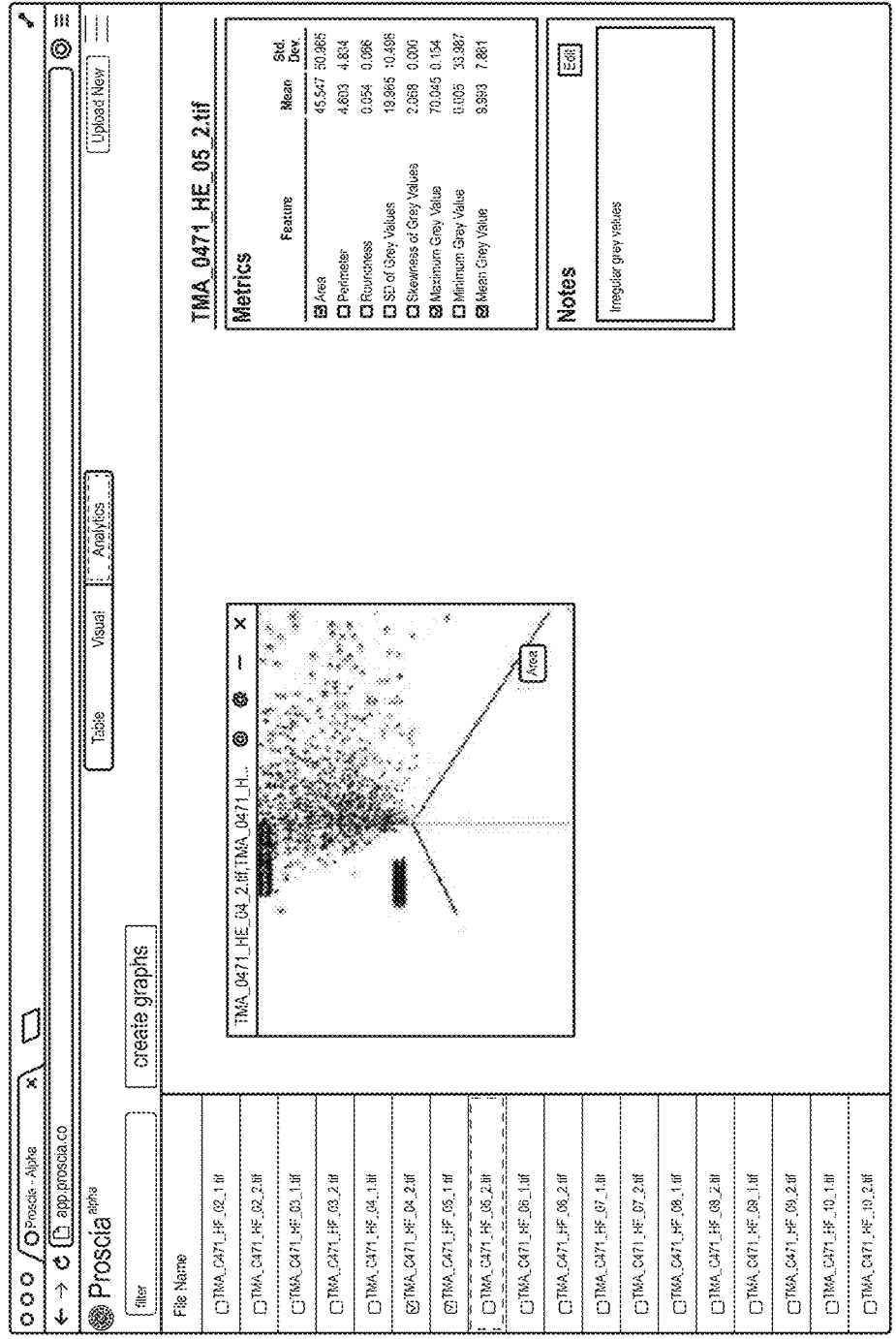

FIG. 12 shows an example embodiment of a user console comprising a measurement tool according to the present disclosure. FIG. 13 shows an example embodiment of a user console comprising a data table according to the present disclosure. FIG. 14 shows an example embodiment of a user console comprising an annotation tool according to the present disclosure. FIG. 15 shows an example embodiment of a user console comprising a run control tool according to the present disclosure. FIGS. 16A-B show a plurality of example embodiments of a plurality of user consoles comprising a plurality of data visualization tools according to the present disclosure.

Data in the computing system 108 may be accessed or one or more processes of the computing system 108 may be controlled by an outside user, such as via a client, or a computer, such as via an artificial intelligence process or function. The computing system 108 enables a user console for a human user to interact with the computing system 108. Although the computing system 108 can be set to open access, the computing system 108 is set to closed access, which can be selective based on a setting set by an administrator of the computing system 108, such as for security, privacy, ease of use, or other purposes. For example, some access controls, such content controls, can be used for controlled or managed access by users of one or more image repositories or one or more UICD repositories, which in some embodiments can be a single repository.

The user console comprises a GUI which may be positioned, situated, hosted, or located within a native application or a web application. The user console comprises a digital tissue slide viewer, a data manager, and a data visualization toolkit, among other features. The user console allows the user to upload or otherwise import new images for quantification, analysis, and hosting. Additionally, the user console can provide access to processes for image and UICD analysis. The present disclosure discloses various visual and descriptive examples of a plurality of components of the user interface. However, note that any functionality of the user interface is not restricted by such examples. Rather, such examples convey many functionalities of the user interface as the user interface relates to the computing system 108.

As shown in FIG. 12, a user console 1200 comprises a measurement tool, which may be used in image viewing in a DZI format. Also shown is an example of UICD image-derived data access, where the measurement tool (represented as a line across a section of a slide image) relies on image metadata to convert image pixel distance in the slide viewer to micron units.

As shown in FIG. 13, a user console 1300 comprises a data table, which may provide an access to UICD data for many images. Note that some or all components of a UICD may be accessible by the user via the user console, where an access control may define which UICD component, if any, can be accessed.

As shown in FIG. 14, a user console 1400 comprises an annotation tool in the slide viewer. The annotation tool enables the user to highlight and comment on areas of interest in large, high resolution images. One or more annotations could be selectively shared to other users via a unique URL. Such annotation data can be stored in a database, as disclosed herein. For example, because annotations involve images to be viewed in the user console and also involve user input, the annotation data falls under response data component of the UICD, and therefore may be stored as part of the UICD in a database, such as the database 808.

As shown in FIG. 15, a user console 1500 comprises a run control tool, which allows the user to run a logic, such as a set of instructions, a function, a route, a script, or a program, on a remote processing circuit, such as a processor remote from a client associated with or operated by the user, or on the user processing circuit, such as a processor local to a client associated with or operated by the user. This logic may manipulate data shown in the user console, or calculate properties of subsets of this data, including, but not limited to Pearson correlation coefficient, covariance, principal components, or others.

As shown in FIGS. 16A-B, a user console 1600A and a user console 1600B comprise a plurality of data visualization tools, which output graphs and charts to represent UICD datasets of varying dimensions.

In some embodiments, an API component of the computing system 108 may be configured to provide same data as provided by the user console, but in one or more extensible, platform-agnostic formats, including, but not limited to XML, JavaScript Object Notation (JSON), and Comma-separated Value (CSV) whether additional or alternative to a visual representation in the user console. Data from the API may be customized, manipulated, or visualized by the user in any way. Further, the API, like the user console, may provides a framework by which the user can run logic, such as a set of instructions, a function, a route, a script, or a program, on a processing circuits remote from the user.

Figure 17:
FIG. 17 shows a flowchart of an example embodiment of a process to maintain a record of a database hardened against tampering or revision according to the present disclosure.

FIG. 17 shows a flowchart of an example embodiment of a process to maintain a record of a database hardened against tampering or revision according to the present disclosure. A process 1700 includes a plurality of blocks 1702-1710. The process 1700 can be performed via the computing system 108. Note that although the blocks 1702-1710 are listed in one order for performance, in other embodiments, the blocks 1702-1710 can be listed in another order for performance. For example, the block 1708 can be performed in parallel with or before the block 1706 or the block 1710 can be performed in parallel with or before the block 1706 or the block 1710. Note that the process 1700 can be applied to any type of content, such as an image, a video, an alphanumeric, a sound, or any other type of content, including any permutation or combination thereof.

In the block 1702, the computing system 108 generates a record in a database. For example, the server 110, such as upon a request from a client, can interface with the controller 112 to create a new record in the storage 114. The new record can contain a plurality of categories for a specific data type or information type. For example, the category can comprise a field. For example, the storage 114 can comprise the database.

In the block 1704, the computing system 108 generates a block chain for a category of the record. For example, the block chain can comprise or represent a ledger, a data structure, or a database storing a continuously growing list of transactions, which are recorded in a chronological order and a linear order, where an authenticity of a transaction should be verified before a block, which contains the transaction, is added to the block chain. Once the block is added to the block chain, then the block generally cannot be removed or modified, even by an operator of the computing system 108. Note that the block chain can be public or private or any combination thereof, as controlled by the computing system 108. Note that the block chain hardens the list against tampering and revision.

Note that the block chain comprises a plurality of blocks, with each of the blocks comprising a time-stamped batch of a transaction, and with each of the blocks comprising a hash of a block prior thereto, thereby linking such two blocks together and forming a chain, with each additional block reinforcing a block before. Note that a transaction comprises content to be stored in the block chain, such as alphanumeric. Transactions are created by participants using the computing system 108, such as accessing the record, such as via reading, writing, or other data operations. Via the computing system 108, a user creates a transaction that is passed between nodes on a best-effort basis. The computing system 108 defines a valid transaction, such as set via an administrator of the computing system 108. Note that a block records and confirms when and in what sequence transactions enter and are logged in the block chain. A blocks is created by a user via a client, which can be a colloquially known as a miner who employs logic to create a block. Note that the block chain can be distributed/decentralized among a plurality of clients, in whole or in part. Note that a transaction can be broadcast to such network using a logic associated with a client. One or more network nodes can validate a transaction, add such transaction to a copy of the block chain associated with a client, and broadcast such addition to other nodes. Note that the block chain can be as a trusted time stamp for one or more messages, such as where a message is stored in the block chain, thereby allowing a client with access to the block chain to read the message. Note that there can be multiple block chains corresponding to or per record, such as one block chain per category of the record. In some embodiments, the block chain corresponds to the record, as a whole, whether additional to or alternative to the block chain corresponding to the category of the record. In some embodiments, there can be a single block chain corresponding to or per at least two records or at least two categories of a single record.

In some embodiments, the computing system 108 can analyze a preexisting record in the database, such as via a content analysis, identify one or more categories in the preexisting record, such as when the preexisting record is organized, unorganized, or comprises raw data, optionally segment, group, or organize the preexisting record according to the one or more categories or associate an identifier with the one or more categories, and generate the block chain for a category of the one or more categories based on the identifier. Note that there can be multiple block chains corresponding to or per preexisting record, such as one block chain per category of the preexisting record. In some embodiments, the block chain corresponds to the preexisting record, as a whole, whether additional to or alternative to the block chain corresponding to the category of the preexisting record. In some embodiments, there can be a single block chain corresponding to or per at least two preexisting records or at least two categories of a single preexisting record.

In the block 1706, the computing system 108 grants an access for the block chain to a client. The access is over a network, such as the network 102. The access comprises reading. In some embodiments, the access comprises writing. In some embodiments, the access comprises modifying or editing. In some embodiments, the access comprises deleting.

In the block 1708, the computing system 108 grants an access for the record to a client. The access is over a network, such as the network 102. The access comprises reading. In some embodiments, the access comprises writing. In some embodiments, the access comprises modifying or editing. In some embodiments, the access comprises deleting.

In the block 1710, the computing system 108 maintains the block chain as the record is accessed. Note that a client can maintain the block chain as the record is accessed, whether the client accesses the record or not. For example, such maintenance may comprise block or transaction processing or broadcast.

In some embodiments, the computing system 108 can be used for powering a clinical trial via a quantitative analysis, such as for early-stage efficacy testing or candidate identification.

Although the present disclosure is described with reference to biological pathology, such as for oncology, genomics, biomarker discovery, or others, the present disclosure can be employed in any field that includes image processing, such as any local or networked service hosting, availing, or distributing any image-based content, such as aerial or satellite imagery, star imagery, material imagery, structural imagery, marine imagery, or others. For example, a bright field microscopy analysis or an assay pipeline can be used for exploratory or retrospective study including biomarker discovery or target identification/validation.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The present disclosure may be embodied in a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language, R programming language or similar programming languages. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable technology including memory sharing, message passing, token passing, network transmission, among others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

Although preferred embodiments have been depicted and described in detail herein, it will be apparent to those skilled in the relevant art that various modifications, additions, substitutions and the like can be made without departing from the spirit of the disclosure, and these are, therefore, considered to be within the scope of the disclosure, as defined in the following claims.

The invention claimed is:

1. A method comprising:
   receiving, via a processor, an image depicting a tissue;
   quantifying, via the processor, the image based on:
   segmenting, via the processor, the image into a plurality of segments;
   identifying, via the processor, a plurality of histological elements in the segments;
   forming, via the processor, a network graph comprising a plurality of nodes, wherein the histological elements correspond to the nodes;
   measuring, via the processor, a feature of the network graph;
   performing, via the processor, a transformation on the image based on the feature;
   determining, via the processor, a non-parametric feature of the image based on the transformation;
   saving, via the processor, the non-parametric feature onto a database.

2. The method of claim 1, wherein the image is a whole slide image.

3. The method of claim 1, wherein the segment depicts at least one of a nucleus, a cell, or a gland.

4. The method of claim 3, wherein the quantifying comprises performing, via the processor, a morphometric process on the at least one of the nucleus, the cell, or the gland, wherein the identifying is based on the morphometric process.

5. The method of claim 1, wherein the transformation is at least one of a Wavelet transformation, a Fourier transformation, or a Chebyshev transformation, wherein the transformation is on the image as a whole.

6. The method of claim 1, wherein the non-parametric feature comprises a signal processing metric.

7. The method of claim 1, further comprising:
   training, via the processor, a machine learning technique based on the non-parametric feature.

8. The method of claim 1, wherein the saving comprises storing, via the processor, the non-parametric feature in a record of the database, wherein the record is associated with the image and with a plurality of images depicting a plurality of tissues, wherein the tissue and the tissues are obtained from a biological entity, wherein the record comprises information about the image and the images, information about a case, and information about an interaction of a user with a server comprising the processor, wherein the interaction is with respect to at least one of the case, the image, wherein the record corresponds to the case.

9. The method of claim 8, further comprising:
   facilitating, via the processor, a maintenance of a block chain for the record.

10. The method of claim 9, wherein the record comprises a category, wherein the maintenance comprises maintaining the block chain for the category, wherein the category is image-based.

11. The method of claim 1, wherein the database is configured to directly interface with a client such that the client is able to request a number of bytes from a location in the database and thereby receive a data of a tile associated with the image.

12. The method of claim 1, wherein the database is an in-memory database.

13. The method of claim 1, further comprising:
   facilitating, via the processor, a maintenance of a block chain for the image.

* * * * *